(12) United States Patent
Bondos et al.

(10) Patent No.: US 11,603,393 B2
(45) Date of Patent: Mar. 14, 2023

(54) SELF-ASSEMBLY OF PROTEIN-BASED BIOMATERIALS WITH MULTIPLE MORPHOLOGIES

(71) Applicant: BONDWELL TECHNOLOGIES LP, College Station, TX (US)

(72) Inventors: Sarah E. Bondos, College Station, TX (US); Alexandra M. Whiteley, Houston, TX (US); Kathleen S. Matthews, Houston, TX (US); Zhao Huang, Houston, TX (US); Autumn Brawley, College Station, TX (US); Jan Patterson, College Station, TX (US)

(73) Assignee: BONDWELL TECHNOLOGIES LP, College Station, TX (US)

( * ) Notice: Subject to any disclaimer, the term of this patent is extended or adjusted under 35 U.S.C. 154(b) by 0 days.

(21) Appl. No.: 17/343,380

(22) Filed: Jun. 9, 2021

(65) Prior Publication Data
US 2022/0033451 A1 Feb. 3, 2022

Related U.S. Application Data

(62) Division of application No. 12/618,518, filed on Nov. 13, 2009, now Pat. No. 11,059,872.

(60) Provisional application No. 61/199,339, filed on Nov. 14, 2008.

(51) Int. Cl.
*C07K 14/47* (2006.01)
(52) U.S. Cl.
CPC .................... *C07K 14/4702* (2013.01)
(58) Field of Classification Search
CPC .................................................. C07K 14/4702
See application file for complete search history.

(56) References Cited

U.S. PATENT DOCUMENTS

| 8,058,613 B2 | 11/2011 | Lou et al. |
| 2008/0233101 A1 | 9/2008 | Sauer |

OTHER PUBLICATIONS

U.S. Appl. No. 12/618,518, Final Office Action, dated Sep. 22, 2020, 10 pages.
U.S. Appl. No. 12/618,518, Notice of Allowance, dated Mar. 11, 2021, 5 pages.
U.S. Appl. No. 12/618,518, Notice of Allowance, dated Oct. 21, 2020, 5 pages.
Adams et al., "The Genome Sequence of *Drosophila melanogaster*", Science, vol. 287, Mar. 24, 2000, pp. 2185-2195.
Beachy et al., "Cooperative Binding of an Ultrabithorax Homeodomain Protein to Nearby and Distinct DNA Sties", Molecular and Cellular Biology, vol. 13, No. 11 Available online at https://www.ncbi.nlm.nih.gov/pmc/articles/PMC364756/, Nov. 1993, pp. 6941-6956.
Chen et al., "Conserved DNA Binding and Self-association Domains of the *Drosophila zeste* Protein", Molecular and Cellular Biology, vol. 12, No. 2, Feb. 1992, pp. 598-608.
Greer et al., "The *Drosophila* Transcription Factor Ultrabithorax Self-Assembles into Protein-Based Biomaterials with Multiple Morphologies", Biomacromolecules, vol. 10, No. 4, Apr. 13, 2009, pp. 829-837.
Liu et al., "Multiple Intrinsically Disordered Sequences Alter DNA Binding by the Homeodomain of the *Drosophila hox* Protein Ultrabithorax", Journal of Biological Chemistry, vol. 283, No. 30, Jul. 25, 2008, pp. 20874-20887.
Lupas et al., "Predicting Coiled Coils from Protein Sequences", Science, vol. 252, No. 5009, May 24, 1991, pp. 1162-1164.
Application No. PCT/US2009/064449, International Preliminary Report on Patentability, dated May 26, 2011, 7 pages.
Application No. PCT/US2009/064449, International Search Report and Written Opinion, dated Sep. 27, 2010, 9 pages.
Tan et al., "Transcription Activation by Ultrabithorax 1b Protein Requires a Predicted α-Helical Region", Biochemistry, vol. 41, Feb. 2002, pp. 2774-2785.

*Primary Examiner* — Amber D Steele
(74) *Attorney, Agent, or Firm* — Kilpatrick Townsend & Stockton LLP

(57) ABSTRACT

The present disclosure relates, in some embodiments, to a composition comprising a biomaterial. A biomaterial may comprise, for example, one or more molecules capable of self-association and/or self-assembly. In some embodiments, a biomaterial may comprise one or more polypeptides and/or proteins. A biomaterial may comprise, for example, two or more self-assembled Ultrabithorax (Ubx) protein molecules. A Ubx protein, in some embodiments, may be any wild type *Drosophila melanogaster* Ultrabithorax protein, including any natural or non-natural isoforms (e.g., alternative splicing isoforms). The present disclosure relates, in some embodiments, to a method of making a biomaterial comprising contacting two or more Ubx protein molecules under conditions that permit self-assembly to form a first fibril and contacting the first fibril to a second fibril.

11 Claims, 10 Drawing Sheets

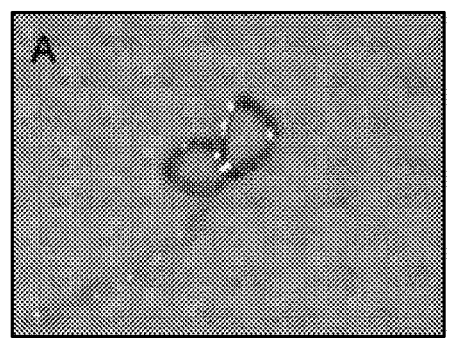
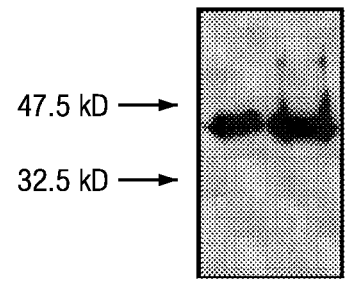
FIG. 2A        FIG. 2B
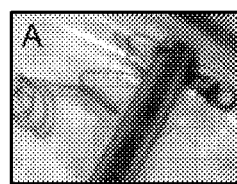 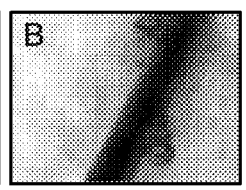 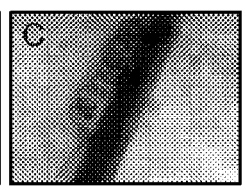
FIG. 3A    FIG. 3B    FIG. 3C
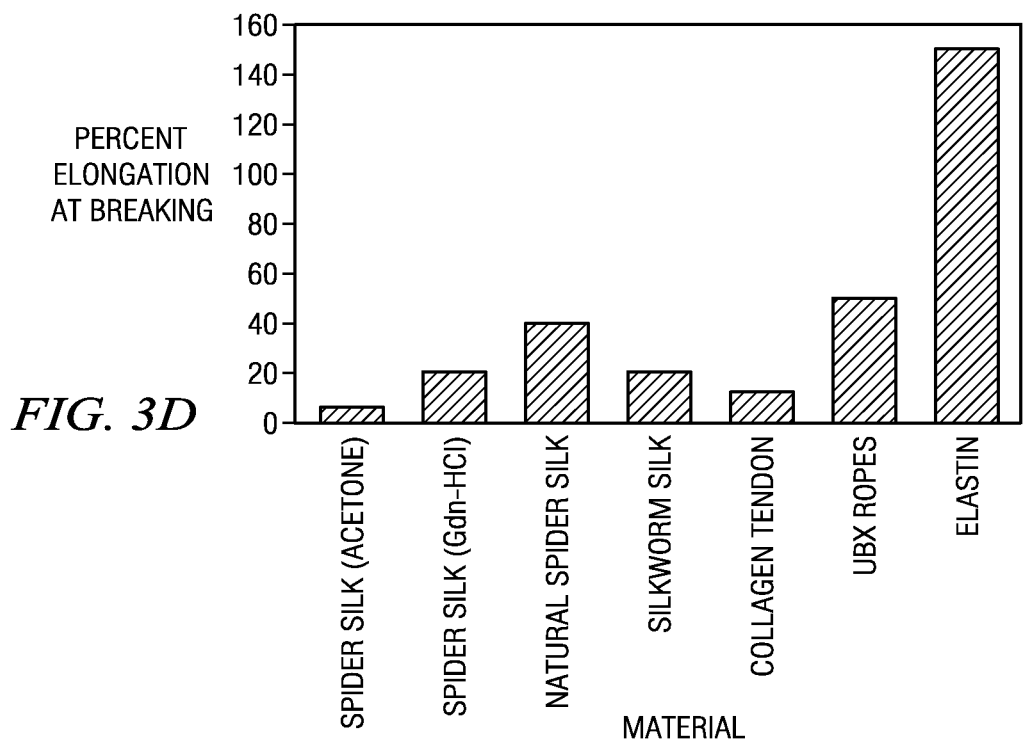
FIG. 3D

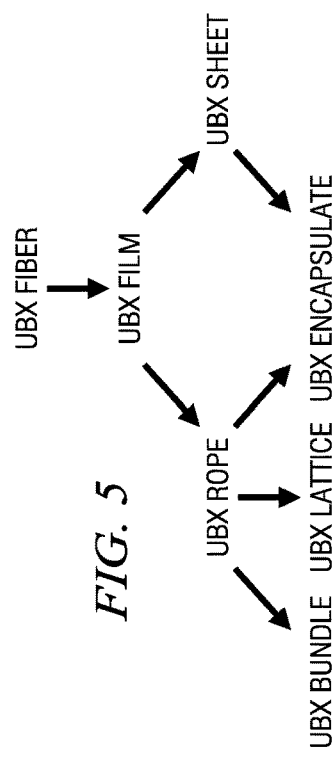
FIG. 5
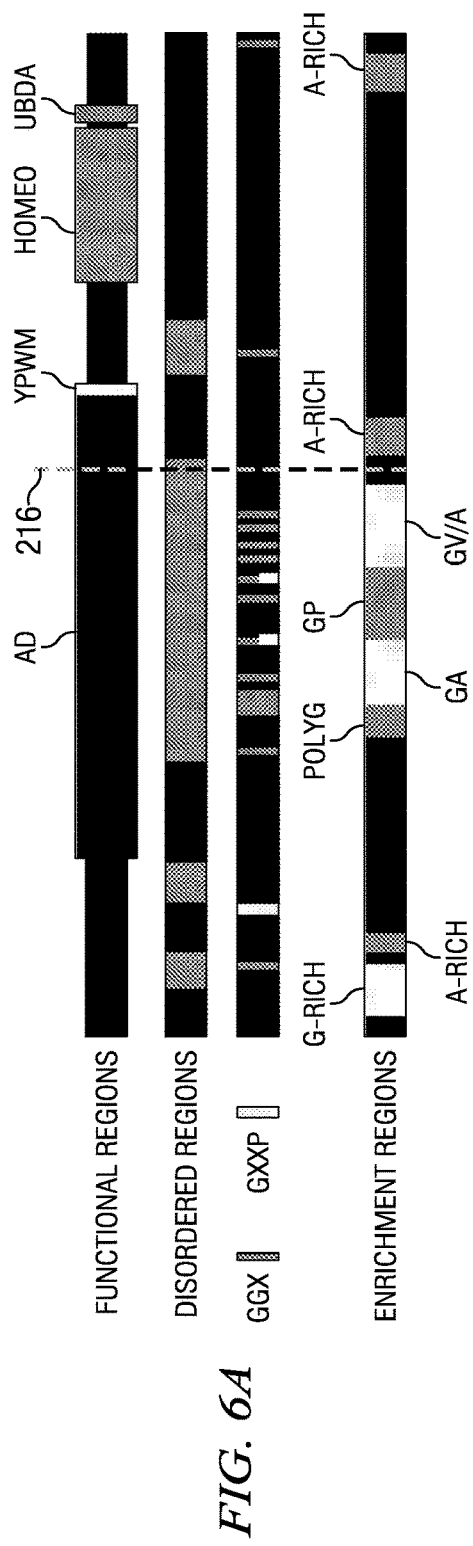
FIG. 6A
FIG. 6C

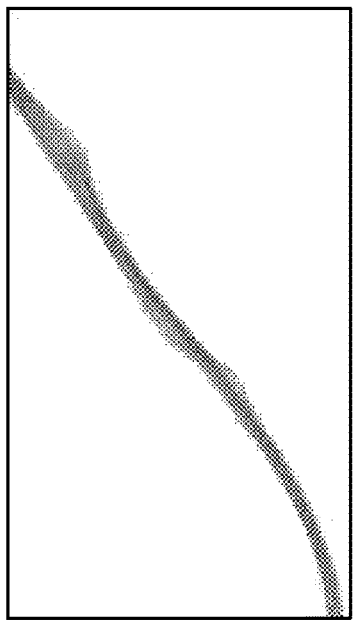
FIG. 10B
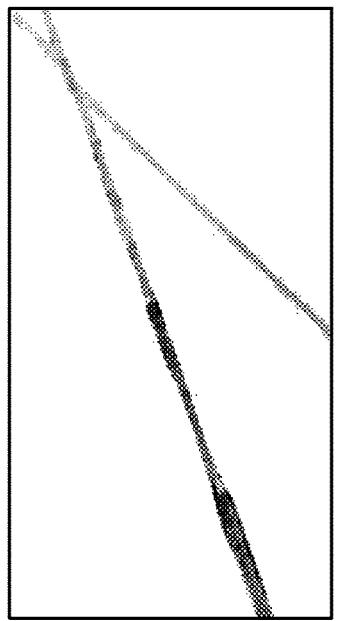
FIG. 10D
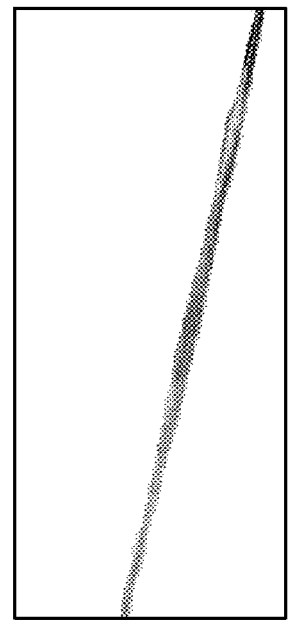
FIG. 10F
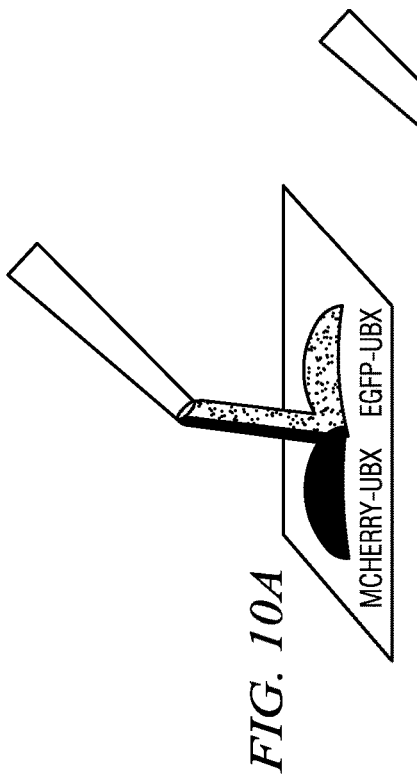
FIG. 10A
FIG. 10C
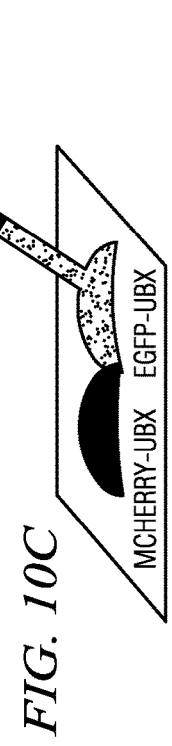
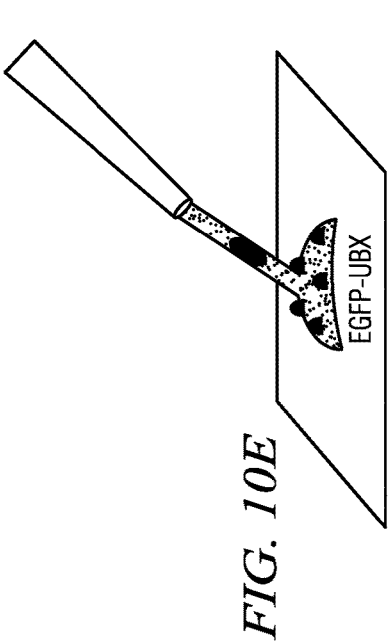
FIG. 10E

SELF-ASSEMBLY OF PROTEIN-BASED BIOMATERIALS WITH MULTIPLE MORPHOLOGIES

CROSS-REFERENCE TO RELATED APPLICATIONS

This application is a divisional of application Ser. No. 12/618,518, filed Nov. 13, 2009, which claims the benefit of U.S. Provisional Application No. 61/199,339 filed Nov. 14, 2008, the full contents of which are hereby incorporated in their entirety by reference.

STATEMENT OF GOVERNMENT INTEREST

This invention was made with government support under National Science Foundation Grant No. 0647452. The government has certain rights in the invention.

FIELD OF THE DISCLOSURE

The present disclosure relates, in some embodiments, to compositions, systems, methods, and articles that include biomaterials (e.g., biomaterials comprising protein capable of self-assembly).

BACKGROUND OF THE DISCLOSURE

Certain proteins and peptides that occur in nature self-assemble into materials with remarkable properties such as elasticity, tensile-strength, toughness, and resilience, or a combination of these or other properties that solve a particular problem faced by an organism. For example, spider dragline silk is the strongest known fiber in nature and gives spiders the ability to dangle safely from an object. Similarly, byssal thread fiber, which elastically fixes mussels to structures in the ocean, is remarkable for its ability to stretch as a wave pulls a mussel away from its position, and then slowly contract, returning the mussel to its original location without damaging it.

Although there has been interest in using these naturally occurring proteins as biomaterials, effective production of engineered materials may face considerable technical issues. Sequence engineering may be limited by length for in vitro synthesized peptides and virtually impossible for materials derived ex vivo. For medical applications, natural materials extracted ex vivo could potentially transfer a disease from the organism to a patient. Production of materials from recombinant monomers produced in E. coli often requires high temperatures or exposure to organic chemicals to stimulate protein assembly. This harsh processing would likely preclude incorporation of active heterologous proteins and thus limit functionalization of the material by genetic methods. Also, initiating protein-based self-assembly often requires high sample concentration and extended times for assembly. Finally, proteins used for self-assembly of superstructures may be incapable of forming multiple higher-order structure shapes or encasing non-conjugated objects.

SUMMARY

Accordingly, a need has arisen for improved building blocks for biomaterials and/or structures comprising biomaterials.

The present disclosure relates, according to some embodiments, to compositions, systems, methods, and articles that include biomaterials (e.g., biomaterials comprising protein capable of self-assembly). In some embodiments, for example, the present disclosure relates to methods for producing biomaterials at reduced concentrations and faster timescale from a recombinant transcription factor Ultrabithorax, a *Drosophila melanogaster* protein not known to form extended oligomers in vivo. A composition of biomaterials, according to some embodiments, may be strong, durable and/or capable of forming higher-order structure shapes for various biomedical uses. In some embodiments, a method may include making a composition of biomaterials that require simpler conditions, lower protein concentration, less time and effort than other engineered biomaterials. The present disclosure further relates to methods of using compositions of biomaterials in biomedical and non-biomedical applications in some embodiments.

According to some embodiments, a biomaterial composition may comprise two or more self-assembled Ultrabithorax (Ubx) protein molecules. A Ubx protein molecule may comprise an amino acid sequence selected from Accession No. AAN13717, Accession No. AAN13718, e Accession No. AAN13719, Accession No. AAF55355, Accession No. AAF55356, and Accession No. AAS65158 in some embodiments. A Ubx protein molecule may comprise, according to some embodiments, a ligand (e.g., labeled markers, growth factors, transcription factors, antibodies, cytokines, hormones, antibiotics, and combinations thereof). For example, a ligand may comprise biotin. In some embodiments, a Ubx protein molecule may comprise a Ubx protein and at least one other protein component (e.g., all or part of an enzyme, an enzyme inhibitor, an antigen, an antibody, a hormone, a coagulation factor, an interferon, a cytokine, a growth factor, differentiation, an osteogenic factor, a bone resorption factor, a cellular motility factor, a bactericidal factor, an antifungal factor, a chemotactic factor, a cytostatic factor, a plasma adhesive molecule, an interstitial adhesive molecule, an extracellular matrix, and a ligand binding factor). A Ubx protein may comprise an amino acid sequence selected from full length Ubx protein (SEQ ID NO:3), Ubx protein (SEQ ID NO:3) missing residues 19-48, Ubx protein (SEQ ID NO:3) comprising residues 216-356, and Ubx protein (SEQ ID NO:3) comprising residues 88-243 in some embodiments. A Ubx protein molecule may comprise, according to some embodiments, a protein having a sequence that is at least 95% identical to full length Ubx protein (SEQ ID NO:3). In some embodiments, a biomaterial composition may form (e.g., be comprised in) a biomaterial structure having a fibril, film, fiber, sheet, bundle, lattice, scaffold or encapsulate morphology. A biomaterial structure may comprise, for example, at least two different Ubx fusion proteins (e.g., a biomaterial composition wherein the structure is a bundle that comprises at least two different Ubx fusion protein fibers).

According to some embodiments of the disclosure, a method of making a biomaterial comprising Ubx may comprise (a) concentrating a Ubx protein solution, (b) exposing the Ubx protein solution to a metal chelator to self-asseble Ubx proteins, and (3) recovering the recovering assembled Ubx material(s) proteins. A metal chelator may be selected from, for example, one or more of ethylenediaminetetraacetic acid (EDTA), (ethylenebis(oxyethylenenitrilo))tetraacetic acid (EGTA), and 1,2-bis(2-aminophenoxy)ethane-N,N,N',N'-tetraacetic acid (BAPTA). A method of making a biomaterial comprising Ubx may further comprise incubating the Ubx protein solution with a metal chelator (e.g., for at least 2 hours) in some embodiments. A biomaterial comprising Ubx formed may have a structure with a fibril, film, fiber, sheet, bundle, lattice, or encapsulate morphology.

In some embodiments, a method of making a biomaterial may comprise contacting two or more Ubx protein molecules under conditions that permit self-assembly to form a first fibril and contacting the first fibril to a second fibril.

A method of using a biomaterial comprising Ubx may comprise, according to some embodiments, (a) preparing a structure comprising Ubx and having a morphology selected from fibril, film, fiber, sheet, bundle, lattice, or encapsulate, and (b) administering the structure to an animal or human in need thereof. In some embodiments, a method may further comprise seeding a structure (e.g., a lattice) with cells to engineer a tissue. A method may further comprise coating a surface of a biological implant with a structure (e.g., a film) in some embodiments. A method may further comprise, according to some embodiments, stacking structures (e.g., fibers) to create porous three dimensional structures and used for filtration. In some embodiments, a method may further comprise using a structure (e.g., a bundle) as a medical suture.

According to some embodiments, a method of preparing a product from one or more reactants may comprise (a) providing a serial fiber having a first domain comprising a first chimera comprising a first Ubx protein and a first catalyst and a second domain comprising a second chimera comprising a second Ubx protein and a second catalyst, wherein the first catalyst is operable to react with at least one reactant to form at least one intermediate and the second catalyst is operable to react with the at least one intermediate to produce the product; (b) contacting a composition comprising the one or more reactants with the first domain of the serial fiber under conditions that permit formation of the at least one intermediate; and/or (c) flowing the composition along the fiber to contact the second domain under conditions that permit formation of the product. In some embodiments, the first catalyst may be a first enzyme, the second catalyst may be a second enzyme, or the first catalyst may be a first enzyme and the second catalyst may be a second enzyme. A first Ubx protein, in some embodiments, may be the same as or different from a second Ubx protein.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

Some embodiments of the disclosure may be understood by referring, in part, to the present disclosure and the accompanying drawings, wherein:

(FIG. 1A) A Ubx fibril, approximately 50 nM in diameter (arrow). (FIG. 1B) Ubx film, formed from self-associating fibrils. (FIG. 1C) Ubx sheet generated by continuing to allow assembly after Ubx film has been formed. (FIG. 1D) A Ubx fiber being pulled from a Ubx film. (FIG. 1E and FIG. 1F) Ubx fiber at low and high magnification, respectively. (FIG. 1G) Ubx fiber, fractured by the SEM beam, splinters into 50 nm fibrils aligned along the main axis (arrow). (FIG. 1H) The free end of a severed fiber shows a solid core.

FIGS. 2A-2B illustrates materials composed of Ubx protein according to specific example embodiments of the disclosure. (FIG. 2A) A Ubx fiber is stained by Izit, a dye that selectively interacts with protein. (FIG. 2B) A western immunoblot identifies similar bands for purified Ubx (lane 1) and the protein contained within Ubx ropes (lanes 2). The positions of molecular weight markers are indicated to the left.

FIGS. 3A-3D illustrates characterization of Ubx materials according to specific example embodiments of the disclosure. (FIG. 3A) A Ubx fiber, stained with Izit dye, and transferred to a phosphate-buffered saline solution attached to a syringe needle prior to heating. (FIG. 3B) The same Ubx fiber after one hour and (FIG. 3C) two hours of heating at 98° C. Ubx ropes do not degrade at high temperatures, demonstrating surprising heat resistance. (FIG. 3D) An example embodiment of a Ubx fiber has an about 53% breaking strain, and thus is more extensible than many protein-based materials.

(FIG. 4A) a bundle composed of six partially melded ropes; (FIG. 4B) a bundle composed of two ropes which completely meld to one another; (FIG. 4C) a twist of two Ubx ropes; (FIG. 4D) the intersection of two ropes in a lattice, which forms a stable interaction; (FIG. 4E) a tethered microencapsulate, formed by drawing a Ubx sheet into a less organized fiber, contains approximately 0.5 µL of buffer; and (FIG. 4F) a microencapsulate, which contains approximately 4 µL if buffer, and is formed by gradual extension of a hanging Ubx drop.

FIG. 5 illustrates a schematic depicting hierarchical assembly of many material architectures from Ubx fibers according to a specific example embodiment of the disclosure.

FIGS. 6A-6C illustrates schematics of Ubx (Accession No. AAN13718; SEQ ID NO: 3) and Ubx deletion mutants showing sequence features according to specific example embodiments. (FIG. 6A) Bar diagrams of Ubx sequence schematic depict overlap between functional domains, regions containing intrinsic disorder, elastomeric motifs and regions enriched in a subset of amino acids. The transcription activation domain (AD), Extradenticle protein interaction motifs (YPWM and UbdA), the alternatively spliced microexons (ME), the homeodomain (HD), and a partial transcription repression domain (RD) are labeled. (FIG. 6B) Ubx sequence schematics of the truncation mutants utilized to locate minimal materials-forming regions. The robustness of the materials is reflected in the average fiber length, after 2 and 4 hours are listed to the left. (FIG. 6C) The sequence of the glycine-rich region (SEQ ID NO: 1), subdivided into four domains based on amino acid prevalence.

(FIG. 7A) The morphology of the stress-strain curves for Ubx materials depends on the diameter of the fibers: A representative curve for narrow fibers less than 10 µm in diameter (black) suggests a largely elastic deformation; a representative curve for wide fibers with a diameter larger than 15 µm (light grey) stretches elastically before yielding to plastic deformation at a strain near 0.2. In contrast, intermediate fibers with a diameter between 10 and 15 µm (white with black outline) exhibit a greater mixture of elastic and plastic deformation. Inset, the initial slope of all three stress-strain curves is similar, indicating that all fibers initially deform elastically. (FIG. 7B) The diameter of Ubx fibers depends on incubation time (all fibers assembled from 500 µg/ml protein) and protein concentration (all fibers incubated for 2 hours). (FIG. 7C) The breaking strength depends on the initial diameter of the fibers. The diameter dependence is markedly different for narrow and wide fibers, with the intermediate fibers having a mixture of the two extremes. (FIG. 7D) Young's modulus was measured during the unloading phase of loading/unloading cycles for both narrow and wide fibers. Again, the diameter dependence was very different for these two groups. (FIG. 7E) Narrow fibers return to their original diameter upon unloading (the line is graphed at x=y), whereas, with larger diameter wider fibers increasingly fail to recover their original shape, a mark of plastic deformation. (FIG. 7F) The breaking strain of wide fibers depends strongly on diameter, an effect greatly reduced for narrow fibers. (FIG. 7G) The yielding strength, at which wide fibers transition from elastic deformation to plastic deformation, is only weakly dependent on diameter.

FIGS. 10A-10E schematically illustrates methods to make faced ropes, serial ropes or mixed ropes using two different fluorescent protein marker-Ubx fusion proteins according to a specific example embodiment of the disclosure. (FIG. 10A) Drops of EGFP-Ubx and mCherry-Ubx are incubated separately for an hour, allowed and incubated for another hour, then bundled ropes are drawn from the region where the drops touch. (FIG. 10B) Photograph of a fiber pulled as described in (FIG. 10A). (FIG. 10C) Drops of EGFP-Ubx and mCherry-Ubx are incubated separately and serial ropes are drawn from each droplet in succession. (FIG. 10D) Photograph of a fiber pulled as described in (FIG. 10C). (FIG. 10E) A large droplet of EGFP-Ubx is incubated, small amounts of mCherry-Ubx are dotted on the droplet surface and left unstirred and mixed ropes are subsequently drawn from the dotted droplet. (FIG. 10F) Photograph of a mixed fiber pulled as described in (FIG. 10E).

DETAILED DESCRIPTION

Figure 1A:
FIGS. 1A-1H illustrates materials formed by Ubx according to specific example embodiments of the disclosure.
Figure 1B:
Figure 1C:
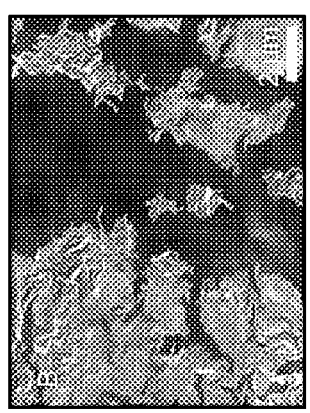
Figure 1D:
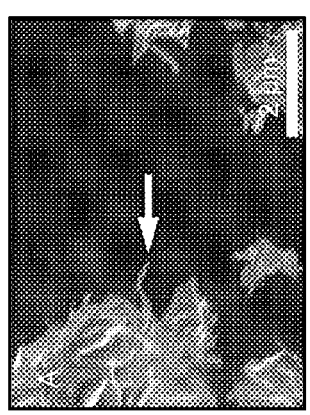
Figure 1E:
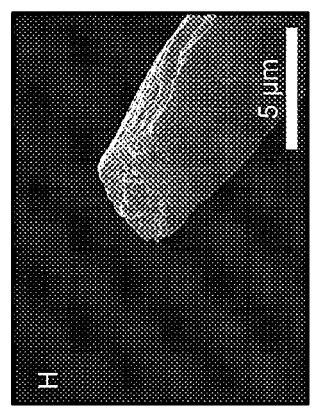
Figure 1F:
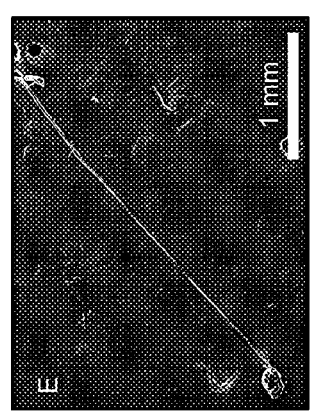
Figure 1G:
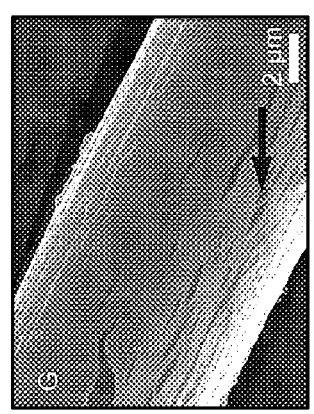
Figure 1H:
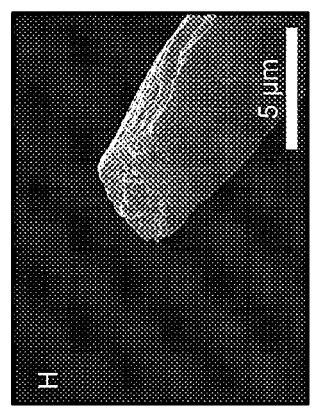
Figure 4C:
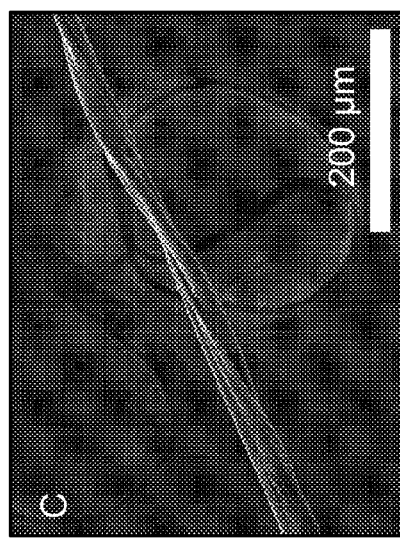
FIGS. 4A-4F illustrates complex architectures formed by Ubx materials according to specific example embodiments of the disclosure.
Figure 4B:
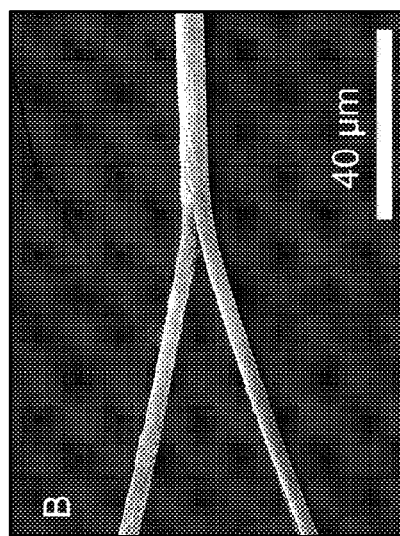
Figure 4A:
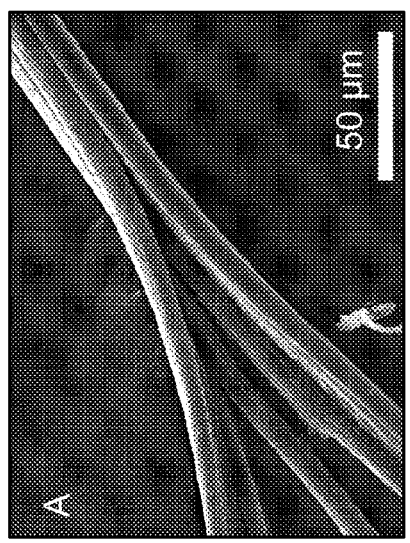
Figure 4F:
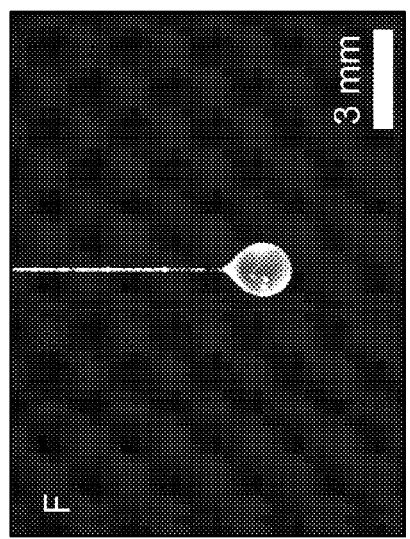
Figure 4E:
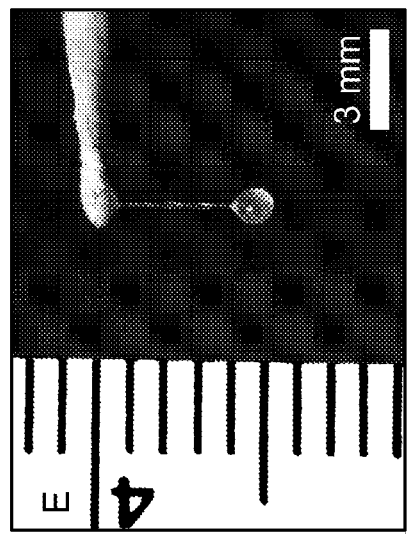
Figure 4D:
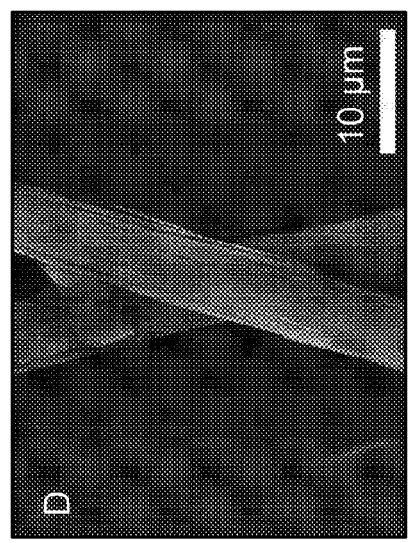

The present disclosure relates, in some embodiments, to compositions, systems, methods, and articles that include biomaterials (e.g., biomaterials comprising protein capable of self-assembly). Biomolecules may have unique chemical and structural properties, which may be arrayed into a macromolecular structure to be used. Complex structures such as fibers, sheets, ropes, bundles, lattices and encapsulates formed from an aggregation of building block biomaterials may have potential applications in, for example, experimental arts, medical arts, nanotechnology arts, and/or material science arts.

For example, protein-based materials may be customized for a variety of advanced applications, including drug delivery, tissue engineering, surgical sealants, medical imaging, biosensors, bionanofabrication, and biomineralization. A variety of materials with different chemical, mechanical, and functional properties may be desired or required for some applications. In some embodiments, for example, macroscale materials for some medical applications may be biodegradeable and/or biocompatible and/or may have mechanical properties matching the tissue(s) of interest. Materials for bionanofabrication, in some embodiments, may form rigid nanoscale three dimensional structures.

Compositions

The present disclosure relates, in some embodiments, to a composition comprising a biomaterial. A biomaterial may comprise, for example, one or more molecules capable of self-association and/or self-assembly. In some embodiments, a biomaterial may comprise one or more polypeptides and/or proteins. A biomaterial may comprise, for example, a Ubx protein. A Ubx protein, in some embodiments, may be any wild type *Drosophila melanogaster* Ultrabithorax protein, including any natural or non-natural isoforms (e.g., alternative splicing isoforms). For example, a Ubx protein may comprise a protein having the amino acid sequence of Accession No. AAN13717, Accession No. AAN13718, Accession No. AAN13719, Accession No. AAF55355, Accession No. AAF55356, and/or Accession No. AAS65158. In some embodiments, a Ubx protein may comprise an amino acid sequence 100% identical to amino acids 88-243 of Accession No. AAN13718, an amino acid sequence 100% identical to amino acids 216 to 356 of Accession No. AAN13718, and combinations thereof. For example, a Ubx protein may comprise an amino acid sequence 100% identical to amino acids 88 to 356. In some embodiments, a Ubx protein may comprise an amino acid sequence 100% identical to amino acids 88-243 and an amino acid sequence 100% identical to amino acids 216 to 356 (both relative to AAN13718) separated by from about 1 to about 50 or more amino acids. The amino acid sequence of amino acids 88-243 may be closer to the amino terminus of a Ubx protein than the amino acid sequence of amino acids 216 to 356 (e.g., as it is in wild-type Ubx) or vice versa, in some embodiments. A Ubx protein, according to some embodiments, may comprise a protein with more than about 60% identity, more than about 70% identity, more than about 80% identity, more than about 90% identity, more than about 95% identity, more than about 98% identity, and/or 100% identical to a sequence selected from Accession No. AAN13717, Accession No. AAN13718, Accession No. AAN13719, Accession No. AAF55355, Accession No. AAF55356, and Accession No. AAS65158. For example, a Ubx protein may be 60% identical to Accession No. AAN13718 but with wild-type amino acid enrichment preserved in intrinsically disordered regions=a.a. 100-130 and the alternatively spliced microexons (a.a. 248-290 in the splicing isoform with Accession No. AAF55355).

According to some embodiments, a Ubx protein may comprise one or more domains that contribute to self-association and/or self-assembly (e.g., interaction and/or binding of the domain with itself and/or another domain or region of a Ubx protein). For example, a Ubx protein may comprise two domains that contribute to self-association and/or self-assembly. In some embodiments, a domain that contributes to self-association and/or self-assembly may be desired and/or required for self-association and/or self-assembly. According to some embodiments, at least one domain for self-association and/or self-assembly may include sequences features found in either amyloidogenic peptides or elastomeric proteins.

According to some embodiments, a Ubx protein may be a full-length Ubx protein or any fragment thereof. Specific lengths of Ubx protein may be generated that include, but are not limited to Ubx 1-380 (full length, AAN13718), Ubx 19-380, Ubx 49-380, Ubx 88-380, Ubx 139-380, Ubx 174-380, Ubx 216-380, Ubx 235-380, Ubx 216-356, Ubx 216-344, Ubx 1-356, Ubx 1-344, Ubx 1-243, Ubx 1-216, Ubx 19-243, Ubx 49-243, Ubx 88-243, and Ubx 139-243. One will appreciate that these fragments are illustrative of some embodiments, and other fragments of Ubx protein may be obtained using the methods described herein. One will also appreciate that one or more properties may differ from fragment to fragment. In some embodiments, it may be desirable to use the full length Ubx protein sequence.

Altering the composition of the Ubx protein (e.g., recombinantly, post-transcriptionally, and/or post-translationally) may be desired in some embodiments in order to impart one or more structural, functional, and/or mechanical properties to the materials. Such properties may include altering the mechanical properties such as altering material strength and/or elasticity. For example, deletions and/or point mutations may be introduced to the Ubx protein to alter one or more structural and/or mechanical properties of Ubx protein fibers and superstructures.

One or more functional properties may be imparted on materials to improve their use in biomedical applications, including, for example, reducing graft rejection, promoting tissue growth, and/or reducing infection. In some embodiments, a biomaterial may comprise a Ubx protein and a ligand (e.g., a ligand that impacts functionality or the structure of Ubx fibers or complex architectures). A ligand may comprise, for example, a labeled marker, a growth factor, a transcription factor, an antibody, a cytokine, a hormone, an antibiotic, and/or combinations thereof. A ligand may comprise biotin, fluorescein, rhodamine, and/or combinations thereof. In some embodiments biotinylated Ubx may be used to create biomaterials in order to bind streptavidin or any of its variants (such as for example avidin). In such embodiments, it may be useful to conjugate streptavidin or any of its variants to other compounds, or molecules that are desired. In some embodiments, biotinylated Ubx may be used to bind a Ubx-containing biomaterial to a structural surface having streptavidin or any of its variants bound thereto.

In some embodiments, a biomaterial comprises a Ubx fusion protein in which a Ubx protein is fused with at least one other protein (e.g., a naturally-occurring protein component having desired structural, mechanical or functional properties to form a chimera). In some other embodiments, a Ubx fusion protein may comprise a Ubx protein and 2, 3, 4, 5, or more than 5 naturally-occurring protein components. A Ubx fusion protein may include, in some embodiments, a Ubx protein with an amino-terminal tag, a carboxy-terminal tag, and/or combinations thereof in some embodiments. A tag may comprise a sequence of from 1 to about 30 or more amino acids.

A fusion protein, in some embodiments, may have a molecular weight of at least about 5 kDa, at least about 10 kDa, at least about 20 kDa, up to about 150 kDa, up to about 200 kDa, and/or up to about 300 kDa or higher. In some embodiments, a Ubx fusion protein containing more than two protein components may be the same or different. In some embodiments, a Ubx fusion protein may have one or more therapeutic properties (e.g., conferred in whole or in part by a non-Ubx portion). A protein in a Ubx fusion protein may comprise all or part of an enzyme, an enzyme inhibitor, an antigen, an antibody, a hormone, a factor involved in the control of coagulation, an interferon, a cytokine, and/or combinations thereof. A cytokine may include, for example, interleukins, interleukin variants which are natural antagonists of their binding to the receptor(s), small induced secreted (SIS) type cytokines, macrophage inflammatory proteins (MIPs). A cytokine may include, for example, a growth factor.

Without limiting the scope of any particular embodiment to a specific mechanism of action, Ubx may, under some conditions, self-associate into fibrils (e.g., nanoscale fibrils) and/or fibrils may self-assemble into higher-order structures such as fibers (e.g., micro-scale fibers), films, sheets, bundles, lattices, or encapsulates. A biomaterial is provided which may permit self-association (e.g., inter-fiber bonding) of a plurality of Ubx fibers to form a complex Ubx structure (e.g., fibril, film, fiber, sheet, bundle, lattice, or encapsulate). In some embodiments where a recombinant Ubx protein is used to form complex architectures, for example, fiber, film, sheet, bundle, lattice, or encapsulate, at least two fibrils of self-associated Ubx protein are included.

Methods of Use

According to some embodiments, a biomaterial may have one or more applications, for example, applications related to its mechanical properties, physical properties, chemical properties, biological properties, or combinations thereof. For example, a biomaterial may have one or more applications related to its ability to assemble complex structures and/or bind ligands. A biomaterial (e.g., a Ubx biomaterial) may be used, in some embodiments, to form an artificial skin graft (e.g., where the biomaterial has properties similar to those of elastin). According to some embodiments, a biomaterial (e.g., a Ubx biomaterial) may be used to supplement and/or replace membranes, fibers, or connections which hold internal organs in place. A biomaterial (e.g., a Ubx biomaterial) may be used as a suture (e.g., a suture that maintains flexibility and/or extensibility during healing) in some embodiments. For example, a biomaterial may be used as a suture in hernia repair or stitches of skin at joints such as elbows or knees. A biomaterial (e.g., a Ubx biomaterial) may be used, according to some embodiments, to form components (e.g., components of class I, II, or III medical devices) which, either alone or in combination with other materials, undergo repeated movements, flexing, and/or stretching.

In some embodiments, a biomaterial (e.g., a Ubx biomaterial) may be used in a scaffold (e.g., a scaffold for tissue engineering). A biomaterial (e.g., a Ubx biomaterial) may self-adhere and/or meld to form complex three-dimensional architectures. Ubx sheets produced in a well may have the dimensions of that well/mold. Stacking sheets with defined two-dimensional shapes may meld the sheets together and produce a three dimensional form. Some embodiments use these Ubx materials as building blocks for facile engineering and functionalization of protein-based materials. The materials described herein may be formed in a variety of complex morphologies, several of which may resemble materials formed by elastomeric proteins.

A biomaterial (e.g., a Ubx biomaterial) may be used in a microencapsulate (e.g., a microencapsulate for controlled drug release and/or transport of a hazardous material) according to some embodiments. A biomaterial (e.g., a Ubx biomaterial) may be used, in some embodiments, to form a porous three dimensional structure (e.g., mesh, lattice, and/or filter). According to some embodiments, a biomaterial (e.g., a Ubx biomaterial) may be used as a glue and/or adhesive (e.g., a biocompatible adhesive).

A biomaterial (e.g., a Ubx biomaterial) may be used to bind a molecule of interest (e.g., a nucleic acid, a protein, a carbohydrate, and/or a lipid) in some embodiments. For example, a Ubx biomaterial may bind the DNA sequence recognized by a Ubx monomer protein (5'-TTAATGG-3') (SEQ ID NO: 2) or related sequences. A nucleic acid-binding biomaterial may be used to separate a nucleic acid of interest from a mixture of components, for example, for preparative, diagnostic, and/or forensic purposes. A biomaterial comprising a biotinylated Ubx protein may be used to separate streptavidin (or any of its variants such as avidin) and anything to which it is bound from a mixture of components. Streptavidin-conjugated materials or their variants may be localized on the surface of a Ubx biomaterial, to provide additional functions to the materials, including but not limited to binding additional ligands or cells, or drug release in some embodiments.

In some embodiments, one may use Ubx chimeras that bind water contaminants to build water filters. Since Ubx materials are thermostable, one could use heat to denature functional protein and release the contaminant for analysis or to regenerate the filter. One could also use functional proteins that degrade water contaminants (e.g., beta-lactamase for penicillin-type antibiotics) to remove organic or biological toxins.

In some embodiments, it is possible to pattern Ubx variants within a material, so that one may also pattern epitopes recognized by nanoparticle-antibody conjugates. Therefore, one could self-assemble microscale to macroscale electronic circuits by patterning conductivity, resistances, etc. One would expect the current from a "Ubx wire" to be related to the density of nanoparticles. Since Ubx ropes may be elastically stretched (maximum size increase=150% (e.g., 10 cm to 25 cm), then one could alter the density of nanoparticles by reversibly pulling on the fiber, turning on or off or tuning the wire.

In some embodiments, a biomaterial (e.g., a Ubx biomaterial) may be used in chemical synthesis. For example, a biomaterial may comprise a catalyst (e.g., an enzyme), for example, as a chimera with a Ubx protein. A biomaterial may be configured to contact a fluid. For example, a biomaterial may be configured as a string suspended from a support. Fluid may be applied to an upper end of the string and allowed to flow in the direction of gravity. For chemical synthesis applications, fluid applied to a biomaterial may comprise a substrate, precursor, co-enzyme, and/or a cofactor. As the fluid flows along a string, it may contact one or more catalysts (e.g., enzyme/Ubx chimeras in the biomaterial) under conditions that permit formation of a product of interest. In some embodiments, a biomaterial may be configured to include two or more different enzymes in a catalytic pathway in some embodiments. Separate purification protocols for each enzyme may be avoided, for example, where purification is based on Ubx or a Ubx-tag. A biomaterial may comprise chimeras arranged in a striped fiber (put a drop of substrate at the top, the drop runs down the fiber and drips off the end as product) or as sheet at the bottom of a series of petri dishes (or a mixed sheet in a single dish if no feedback inhibition loops).

According to some embodiments, a molecule capable of self-association and/or self-assembly may be used to build a three-dimensional structure, make a chimera with active functional proteins, and/or pattern Ubx variants within a material (e.g., bundles with striped fluorescent fibers in which the colors are aligned to create uniformly striped bundles or offset to make a checkerboard pattern). For example, a scaffold may be prepared with sheets in which a portion of each sheet includes a portion instructing nerve formation by stacking each sheet such that these portions aligned to create a path for nerve growth (or vaculature or larger structural features).

A molecule capable of self-association and/or self-assembly may be used to build a scaffold shaped like an organ. A scaffold may include (e.g., in chimeric scaffold molecules) spatio-temporal instructions to cells infiltrating the scaffold. In some embodiments, a method of making a scaffold may comprise constructing Ubx sheets in molds shaped like serial cross-sections of an organ and/or stacking the sheets to build the organ scaffold. A method of making a scaffold may comprise, according to some embodiments, (1) altering two-dimensional arrangement of monomers when making sheets and/or (2) leaving holds and plugging in or threading through materials made from an alternate chimera. Different chimeras may be used to provide signals or release diffusible signals instructing cell migration, growth, and differentiation. A method of making a scaffold may comprise configuring and arranging one or more chimeras that release a ligand to define or alter the interaction interface, for example, to speed or slow release, thereby providing a timed sequence of instructions.

A biomaterial (e.g., a Ubx biomaterial) may be used, in some embodiments, to form a neurovascular bundle. Nerves may occur adjacent to vasculature. A 2-fiber Ubx bundle comprising one fiber with one or more components that stimulate nerve growth and one or more components that stimulate vascular epithelial cells may be used, in some embodiments, to assemble nerve cells and vascular epithelial cells into adjacent lines and then tubes. Optionally, other materials may be conjugated to Ubx bundles such as for example, growth regulators and/or survival factors.

Methods of Making

The present disclosure relates further to methods of forming a biomaterial (e.g., a biomaterial comprising a Ubx protein). The present disclosure also relates to a DNA vector capable of expressing a recombinant Ubx protein. In some embodiments, a Ubx vector expressed in a suitable host serves as a source of a Ubx protein. A vector may be adapted for expression in a cell, for example *E. coli*, and comprises DNA sequences encoding Ubx and regulatory elements needed for expressing Ubx proteins. In some embodiments, a DNA vector may contain sequences for peptide tags for use in purification or to provide additional function(s), or an additional gene, capable of expressing a non-Ubx protein and further modifying Ubx structures. In another related embodiment, the DNA vector would be inserted into a host cell, for example *E. coli* for expression.

According to some embodiments, a vector may be inserted into a host cell that is insect, mammalian, bacterial or plant in origin where the vector is engineered to express Ubx proteins that are appropriate for the host cell used. In some embodiments where truncated Ubx proteins are desired, it is possible to generate C-terminal truncations by inserting one or more stop codons into a Ubx coding region. Methods to insert stop codons are known in the art and include for example site-directed mutagenesis. Methods for making substitution mutations at predetermined sites in DNA having a known sequence may include, for example, M13 primer mutagenesis and/or polymerase chain reaction (PCR) techniques.

In some embodiments of the disclosure, a recombinant Ubx protein containing at least one minimal domain required for self-assembly of Ubx, may be expressed and purified. A Ubx protein, according to some embodiments, may be grown and/or isolated and purified.

According to some embodiments, the concentration of Ubx protein required for self-assembly and the time required to generate protein-based materials may be lower than the concentration and time required for assembly of spider silk protein, amyloid proteins, human prion protein, and/or resilin protein fragment as shown in Table 1.

TABLE 1

Comparison of protein concentrations required and concentrations used to generate protein-based materials.

| Protein | Concentration (mg/ml) | Cosolvent or method | Time |
|---|---|---|---|
| Ubx | 0.075 | Aqueous, pH 8 | 2 hours |
| Proteins obtained ex vivo | | | |
| Spider silk | 300-500 | Methanol | |
| Silkworm silk | 58-170 | Methanol, HFIP | |
| Recombinant elastometric proteins | | | |
| Resilin protein fragment | >100 | Cross-linking agents | |
| Spider silk protein fragment | 12.5 | Organic solvent | |
| Spider silk protein ADF-3 | 100-280 | Methanol | |
| Spider silk nanofibers | 5-30 | Methanol | 1 week |
| Spider silk-like protein-machine drawn[1] | 250-300 | HFIP | |
| Spider silk-like protein-hand drawn | 7-10 | Aqueous | |
| Amyloid proteins/peptides | | | |
| Amyloid peptide fibrils | 10 | Low pH, acetonitrile | 1 week |
| β-lactoglobulin | 83-138 | Low pH, high temperature or alcohol/TFE | |
| Human prion protein | 0.03 | Metal ions | Days |

[1]Protein purified by heat precipitation of contaminants
HFIP = hexafluoroisopropanol According to some embodiments, a biomaterial may be formed by contacting a first molecule of Ubx with a second molecule of Ubx under conditions which permit self-association (e.g., intermolecular bonding) of the first and second Ubx molecules to form a dimer. Such contacting may be repeated to form a Ubx fibril. A biomaterial may be formed, in some embodiments, by contacting a first Ubx fibril with a second Ubx fibril under conditions which permit self-association (e.g., inter-fibril bonding) of the first and second Ubx fibrils to form a complex Ubx structure (e.g., fiber, film, sheet, bundle, lattice, or encapsulate). In some embodiments where a recombinant Ubx protein is used to form complex architectures, for example, fibers, film, sheet, bundle, lattice, or encapsulate, at least two fibrils of self-associated Ubx protein are used.

Without limiting the scope of any particular embodiment to a specific mechanism of action, Ubx may, under some conditions, self-associate into fibrils and/or fibers may self-assemble into higher-order structures. A constituent Ubx protein may have dual properties such that one portion of the protein is capable of forming short fibrils, whereas the other portion interacts with other copies of itself, driving the fibrils to self-associate into larger structures. A hierarchical assembly of Ubx material according to some embodiments of the disclosure is shown in FIG. 5. Ubx fibers, film and sheets may form spontaneously at an air-water interface. Construction of other structures may require external forces. Ubx ropes may be drawn from a film. More complex architectures (bottom row) are composed of sheets and/or ropes and may be constructed by hand or by gravity.

A method of preparing a biomaterial may comprise, in some embodiments, (a) concentrating a Ubx protein solution, (b) exposing the Ubx protein solution to a metal chelator, and/or (c) recovering assembled Ubx material(s). In some embodiments, concentrating a Ubx protein solution includes using methods generally available to concentrate protein solutions. Ubx protein concentration, in some embodiments, may be from about 0.001 to about 1.0 mg/ml, from about 0.010 to about 0.500 mg/ml, from about 0.025 to about 0.200 mg/ml, and/or from about 0.050 to about 0.100 mg/ml. For example, Ubx protein concentration may be 0.075 mg/ml.

In some embodiments, Ubx oligomerizes in the presence of non-denaturing aqueous solution near neutral pH (e.g., between about 6.0 and about 8.0, between about 6.5 and about 7.5, or about 7.0) at temperatures near or below about 25° C. (e.g., between about 4° C. and about 25° C. and/or between about 10° C. and about 20° C.). In some embodiments, Ubx self-assembles into fibers in between about 1-5 hours and in some embodiments, between 2 and 4 hours. In some embodiments, Ubx self-assembles in less than about 10 hours, less than about 8 hours, less than about 6 hours, less than about 4 hours, less than about 3 hours, less than about 2 hours, and/or less than about 1 hour. According to some embodiments, it may be desirable to allow self-assembly to proceed for longer periods of time (e.g., 3 days).

In some embodiments, exposing a Ubx protein to a metal chelator includes adding an effective amount of metal chelator to promote assembly of Ubx proteins. Addition of a small amount of metal chelator to a Ubx solution may aid fiber formation and/or prevent amorphous aggregate formation. Suitable metal chelators include, but are not limited to EDTA, EGTA, BAPTA and combinations thereof. In some embodiments, a metal chelator may be present at a concentration of between about 2 mM and 30 mM. In some embodiments, a metal chelator may be present at a final concentration of between about 5 mM and 20 mM. In some embodiments, a metal chelator may be present at a final concentration of between about 8 mM and 15 mM. In some embodiments, a metal chelator may be present at a final concentration of about 10 mM. According to some embodiments, the ability of Ubx to form materials may be affected by the kind and/or amount of buffer present. In some embodiments, a salt may be present at a concentration of between about 100 mM and 500 mM. In some embodiments, a salt may be present at a concentration of between about 200 mM and 400 mM. In some embodiments, a salt may be present at a concentration of about 300 mM NaCl.

A composition for assembly of a Ubx protein (e.g., in a motor method) may comprise, according to some embodiments, 5% glucose (w/v), 500 mM NaCl, and 50 mM sodium phosphate at pH=8.0. A composition for assembly of a Ubx protein (e.g., in a sitting drop method) may comprise, in some embodiments, 5% glucose (w/v), 500 mM NaCl, 200 mM imidazole, and 50 mM sodium phosphate at pH=8.0

In some embodiments, recovering an assembled Ubx material includes allowing an effective amount of time to pass for Ubx proteins to form at the air-water interface and recovering the proteins using a recovery method appropriate to maintain the structure desired. In some embodiments, where a film is desired, a recovery method may include contacting the air-water interface of the solution of Ubx proteins with, for example, a frame, or surface for the film to adhere to in order to pick up the film. A film recovery method may comprise, for example, reshaping a paperclip to form a "U" with a handle, placing one edge of the "U" on the surface and then sweeping the second edge down and lifting the paperclip away from the surface. Film may also be wound around a paper clip. In some embodiments, where a fiber is desired, a recovery method may include contacting the air-water interface of the solution of Ubx proteins with a pointed tip, such as a needle, or pipet tip, to slowly withdraw fibers of Ubx protein for example. In some embodiments, where a sheet is desired, a recovery method may include contacting the air-water interface of the solution of Ubx proteins with a frame, or surface for the sheet to adhere to in order to pick up sheets of Ubx protein, for example. In some embodiments, where a lattice is desired, a recovery method may include contacting the air-water interface of the solution of Ubx proteins with a support having a plurality of arms where fibers of Ubx proteins may be slowly wound around parallel arms such that the fibers intersect between the plurality of arms for example. A single fiber may be wound around a support with two arms such that fibers that intersect meld to one another. In some embodiments, where a bundle is desired, a recovery method may include contacting the air-water interface of the solution of Ubx proteins with a support having a plurality of arms where a plurality of fibers of Ubx proteins may be placed in parallel and then dipped into a drop of water and slowly withdrawn from the water to cause bundling of the plurality of fibers, for example. In some embodiments, where a tethered encapsulate or microbasket is desired, a recovery method may include allowing a sheet to form as described above and then contacting the air-water interface of the solution of Ubx proteins with a pointed tip and withdraw the tip slowly resulting in a tethered encapsulate for example. Other equivalent recovery methods may be used that follow the same mechanical principles for recovery of the Ubx structures as described herein. For example, tethered encapsulates alternatively may form spontaneously during slow extrusion of Ubx protein solution through a two-way stopcock for example.

In some embodiments, a solution of Ubx protein may be allowed to self-assemble by placing a concentrated Ubx protein solution in a covered chamber (e.g., to reduce the effects of evaporation on a Ubx solution) undisturbed for several hours. In some embodiments, a covered chamber may have controlled and/or regulated humidity to reduce evaporation of a Ubx solution. In some embodiments, Ubx fibers that form from a Ubx solution may be between about 10 and about 70 nm wide, between about 20 and about 60 nm wide, between about 30 and about 50 nM wide, and/or about 50 nm wide. Fibers having other widths are also possible.

As will be understood by those skilled in the art who have the benefit of the instant disclosure, other equivalent or alternative compositions, methods, and systems for making and using Ubx-containing biomaterials can be envisioned without departing from the description contained herein. Accordingly, the manner of carrying out the disclosure as shown and described is to be construed as illustrative only.

Persons skilled in the art may make various changes in the shape, size, number, and/or arrangement of parts without departing from the scope of the instant disclosure. Also, where ranges have been provided, the disclosed endpoints may be treated as exact and/or approximations as desired or demanded by the particular embodiment. Where the endpoints are approximate, the degree of flexibility may vary in proportion to the order of magnitude of the range. For example, a range of endpoint of about 50 may one the one hand include 50.5, but not 52.5 or 55 in the context of a range of about 5 to about 50 and, on the other hand, include 55, but not 60 or 75 in the context of a range of about 0.5 to about 50. In addition, it may be desirable, in some embodiments, to mix and match range endpoints. Also, in some embodiments, each figure disclosed (e.g., in one or more of the Examples and/or Drawings) may form the basis of a range (e.g., +/−about 10%, +/−about 100%) and/or a range endpoint. Persons skilled in the art may make various changes in methods of preparing and using a composition, device, and/or system of the disclosure. For example, a composition, device, and/or system may be prepared and or used as appropriate for animal and/or human use (e.g., with regard to sanitary, infectivity, safety, toxicity, biometric, and other considerations). These equivalents and alternatives along with obvious changes and modifications are intended to be included within the scope of the present disclosure. Accordingly, the foregoing disclosure is intended to be illustrative, but not limiting, of the scope of the disclosure as illustrated by the following claims.

EXAMPLES

Some specific example embodiments of the disclosure may be illustrated by one or more of the examples provided herein.

Example 1

Plasmid Construction of Ubx and Deletion Mutants

Ubx splicing isoform Ia (Accession No. AAN13718; herein termed "Ubx") and Ubx variants were cloned between the NdeI and BamHI sites in the pET19b vector (Novagen), which appends a His-tag to the N-terminus of Ubx. To generate C-terminal truncations, two consecutive stop codons were inserted into the Ubx coding region using the QuickChange site-directed mutagenesis kit (Stratagene).

Example 2

Expression and Purification of Ubx and Ubx Variants

Plasmid constructs were transformed into BL21 (DE3) pLysS *E. coli* cells. *E. coli* cultures were cultivated in Luria broth plus 50 mg/ml carbenicillin and 30 mg/ml chloramphenicol (LB+carb) at 37° C. For expression, 10 ml of an overnight culture, inoculated from a single colony, was used to inoculate a 1 L LB culture which was grown until the absorbance at 600 nm was between 0.6-0.8. Cell cultures were then cooled to 30° C., induced with 1 mM IPTG, and grown for a further 105 mins. Cells were harvested by centrifugation at 7000×g for 15 min. and stored at −20° C. in aliquots corresponding to 1 L of culture. Each aliquot was thawed at room temperature and lysed in 20 ml of lysis buffer 50 mM $NaH_2PO_4$, pH 8.0, 5% glucose w/v, 500 ml NaCl, 1 protease inhibitor tablet (Roche), 0.8 mg/L DNase I). Cell lysates were centrifuged at 18000×g for 20 min. The supernatant was loaded on a nickel-nitrilotriacetic acid (Ni-NTA) agarose resin column (Qiagen), which was pre-equilibrated with 20 ml of equilibration buffer (5% glucose w/v, 500 ml NaCl, 50 mM $NaH_2PO_4$ pH 8.0). The column was then washed by 10, 10 and 5 column volumes of W1, W2 and W3 buffer (20 mM, 40 mM and 80 mM imidazole, respectively, dissolved in equilibration buffer). Protein was eluted with 10 ml of elution buffer (200 mM imidazole dissolved in equilibration buffer). The concentrations of the purified Ubx samples were determined using the BioRad protein assay (BioRad). Approximately 10 mg of DTT was added to each 1 ml elution to maintain the protein in the reduced state. Purified Ubx was dialyzed into storage buffer (300 mM NaCl, 50 mM $NaH_2PO_4$, 5% glucose, 1 mM DTT pH 7.5) before storage at −80° C.

Example 3

Production of Ubx-Based Materials

Ubx film. Ubx was diluted to 300 μg/ml using elution buffer. Ethylenediaminetetracetic acid (EDTA) was added to 10 mM to prevent amorphous aggregation unless otherwise stated. Ubx solution (100 ml) was placed at the surface of a siliconized coverslip at room temperature. Ubx film spontaneously forms at the air-water interface after approximately 1 hour.

In an alternate method, Ubx is pipeted into a reservoir of buffer containing 200 ml to 4 L of assembly buffer (5% glucose, 500 mM NaCl, 50 mM sodium phosphate pH=8.0). After approximately 4 hours, film will form on the surface. This system avoids the dehydration problems mentioned above, and thus film can be allowed to assemble for several days.

Ubx fiber. A needle or pipet tip was used to contact the surface of Ubx film produced either on a siliconized coverslip or a buffer reservoir and withdrawn slowly to draw ropes.

Ubx sheet. Ubx protein samples were concentrated to 1 mg/ml using Vivaspin concentrators with a 10 kD cut off (Viva Science). EDTA was added to a final concentration of 10 mM. Ubx solution (100 ml) was placed at the surface of a siliconized coverslip, and covered with a plastic tube lid to deter evaporation. Ubx sheets formed spontaneously at the air-buffer interface at room temperature overnight.

Ubx lattices. The outer turn of a paper clip, in which the inside turn had been bent out of the way, was used as a support for lattice construction. Ubx ropes were wound around the parallel arms of an opended paper clip such that the ropes intersect between the supporting arms. Freshly made Ubx ropes would adhere to both the metal supports and to each other, forming a lattice. Lattices maintain their form after removal from the supports after 24 hours of drying in air.

Ubx bundle. A 20 ml drop of deionized water was placed on the surface of a siliconized cover slip. A series of Ubx ropes were placed in parallel, approximately 1 mm apart, on the paper clip support, and subsequently dipped into the drop of water. Upon slow withdrawal, the ropes adhered to each other, forming a bundle that consists of multiple ropes. The degree to which the ropes fuse in the bundle appears to be dependent on the age of the fiber.

Ubx tethered encapsulates: microbaskets. Ubx sheet were prepared as described. Objects with sharp ends (pipette tip, needle etc.) was used to make contact with the surface of the sheet and slowly withdrawn to produce mini-encapsulated baskets.

Ubx tethered encapsulates: macrobaskets. Ubx macro-encapsulated baskets form spontaneously during extremely slow extrusion of a purified Ubx (>2 mg/ml) through a plastic two-way stopcock.

Example 4

Characterization of Ubx

Izit Stain. Izit stain (1 ml) was added to 100 mL of eluted protein on a slide and left for 1-2 hours for fibers to form. Ropes pulled from these drops were tinted blue whereas exhausted drops (i.e., all protein in the drop was pulled into ropes) lacked blue color.

SEM imaging. Ubx ropes, lattices and bundles were transferred to the surface of double-sided carbon tape attached to SEM specimen mount stubs. Ubx sheets and ropes were transferred using a needle, whereas Ubx film was carefully lifted using plastic coated wire bent into a stem-loop shape. Samples were sputter coated with gold for 1 min at 100 mA and examined either using an FEI-XL30 environmental scanning electron microscope or an FEI Quanta 400 field emission scanning electron microscope, each with a beam voltage of 200 kV and a spot size of 3.

Western Blot analysis. Ubx ropes were solubilized in 4× sample buffer (250 mM Tris, 40% glycerol, 4% SDS, 4% BME, 0.02 mg/ml bromophenol blue, pH 6.8) by mechanical disruption with a syringe needle followed by repeated cycles of heating (90° C. for 30 min.), vortexing, and sonication (1 minute intervals), with the entire process requiring approximately 2 hours. Ubx monomeric protein was diluted with 4× sample buffer to generate a positive control. Samples were separated using a 12% 29:1 polyacrylamide gel prior to transfer at 150 V for 20 min to a nitrocellulose membrane (Schleicher & Schuell). Ubx was detected using FP3.38 as the primary antibody at a 1:200 dilution in phosphate buffered saline. This antibody is sufficiently specific for the Ubx homeodomain sequence to be used extensively in immunohistochemistry experiments in vivo, demonstrating low cross-reactivity to other proteins with the exception of AbdA, which has nearly the same homeodomain amino acid sequence but was not present in this assay. Horseradish peroxidase conjugated goat anti-mouse antibody (Calbiochem, 1:2000 dilution) was used as the secondary antibody.

Example 5

Materials-Forming Conditions

Most recombinant proteins require harsh conditions to trigger materials assembly, including exposure to high temperatures, organic solvents, pH extremes, or metals. Such conditions would be expected to denature and possibly aggregate many proteins. In distinct contrast, Ubx oligomerizes in non-denaturing aqueous solution near neutral pH at either room temperature or 4° C. Furthermore, Ubx self-assembles into fibers visible by SEM much more rapidly (2 hours) than amyloidogeneic proteins, which typically require days to weeks. Finally, Ubx readily forms materials at protein 0.3 mg/ml, a concentration 1-2 orders of magnitude lower than most other protein-based materials thus reducing the stringent requirements on protein expression and purification for materials generation. The conditions typically utilized to trigger amyloid or elastomeric protein assembly actually inhibit generation of Ubx-based materials. The unusually facile assembly of Ubx into materials reflects reduced thermodynamic barriers for materials formation relative to other protein systems.

Example 6

Experimental Identification of the Minimal Materials-Forming Domains

Figure 6B:
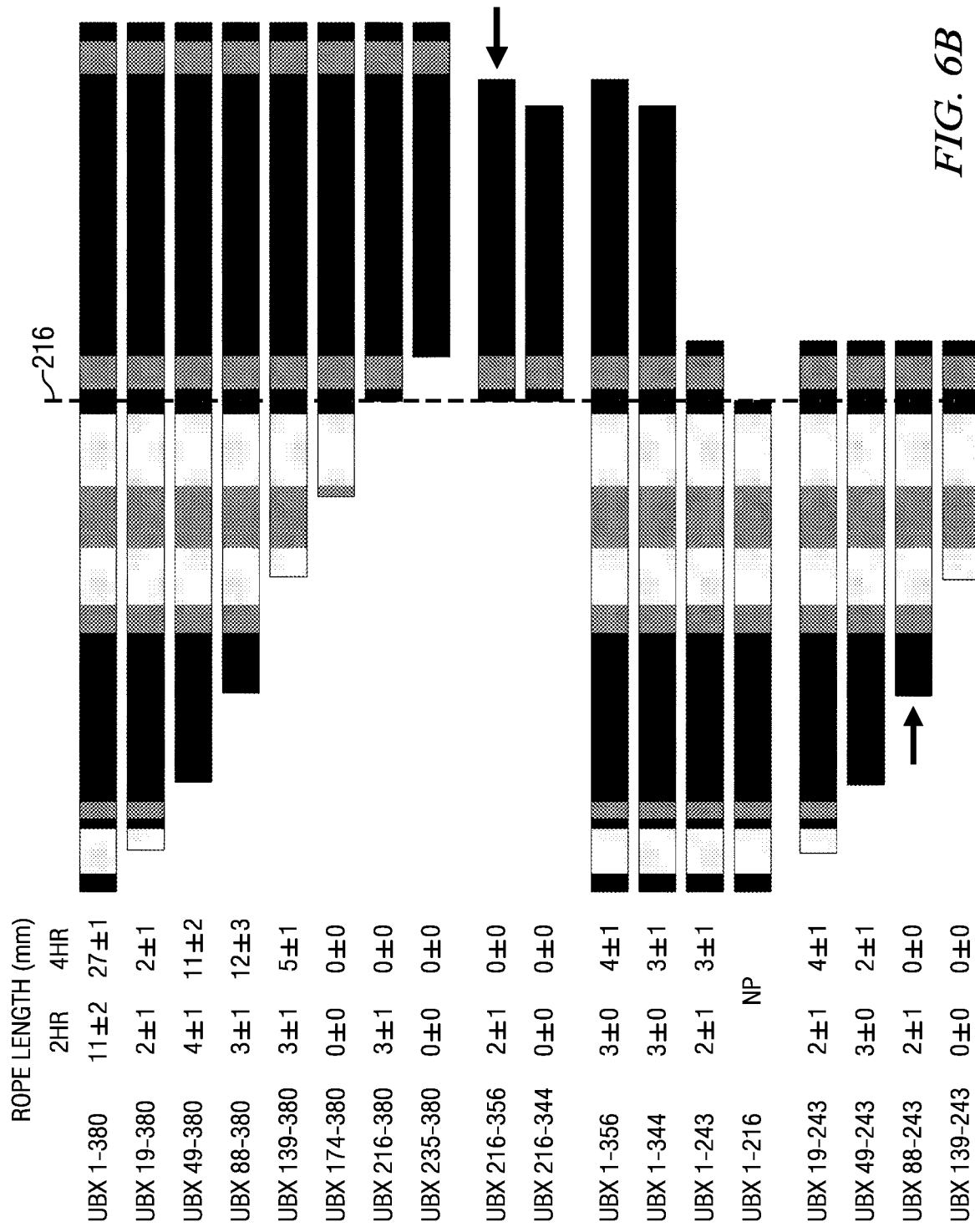

Because Ubx may be produced as a recombinant protein in E. coli, regions have been identified that may be desired and/or required for materials assembly ("minimal materials-forming domains") by examining the ability of Ubx truncation mutants to form ropes. All N-terminal and C-terminal Ubx deletion mutants produce soluble, active proteins and, for mutants encompassing the homeodomain, are capable of binding DNA. Each variant is named for the amino acids included; for instance, the Ubx19-380 mutant includes a histidine tag, the initial methionine, and amino acids Ubx19-380. Boundaries for the truncation mutants bisect neither potential secondary structural elements nor evolutionarily conserved motifs (FIG. 6B). Because some truncation mutants formed materials at a slower rate, each protein was tested for film/fiber formation after 2 and 4 hours of sessile drop incubation on a siliconized coverslip at room temperature. Full length Ubx may form materials after a two-hour incubation, and the slowest truncation mutants capable of forming materials will have assembled within four hours at room temperature. In general, Ubx variants either generated robust materials comparable to full-length protein (>1 cm in length), or produced brittle and therefore short (<5 mm) ropes.

Deleting first from the N-terminus, it was discovered that Ubx19-380 forms short, brittle ropes (FIG. 6B). Surprisingly, this effect is ameliorated in Ubx49-380, Ubx88-380, and Ubx139-380, which all form robust materials, although they require a longer incubation time to do so. Removal of amino acids 2-18 exposes a region that impedes Ubx-Ubx interactions. Residues 19-48 either comprise this inhibition region or are required for its function, since removal of this segment restores the ability to form robust materials.

Surprisingly, Ubx139-380 and Ubx216-380 both form materials, even though these truncations remove either a portion or all of the sequences resembling elastomeric proteins. However, these truncations are difficult to draw, producing shorter, more brittle ropes than Ubx49-380 and Ubx88-380. Ubx variants with further deletions from the N-terminus did not produce materials, marking amino acid 216 as the N-terminal boundary of the minimal materials forming unit.

Even though Ubx139-380 and Ubx216-380 both generate brittle ropes, Ubx174-380, the intermediate truncation, does not form materials. Thus, removal of residues 139-173 exposes a second region of Ubx that inhibits materials assembly. Removal of this inhibitory region in the Ubx216-380 variant restores materials formation. Since much of the region between amino acids 173 and 215 is intrinsically disordered (FIG. 6A), the motion of this highly flexible region may physically block Ubx-Ubx interactions. Indeed, monomeric Ubx174-380 also binds DNA with an affinity more than 20-fold poorer than the full-length protein (Liu 2008), an inhibition largely absent in Ubx216-380. Therefore, amino acids 173-216 debilitate multiple Ubx macromolecular interactions.

The C-terminus of the minimal unit was identified by making progressive deletions from the C-terminal end of the Ubx216-380 variant, the smallest N-terminal truncation mutant which still forms materials (FIG. 6B). Ubx216-356 does form materials even though a poly-alanine region, a key motif in spider silks, was removed. In contrast, Ubx216-344, which additionally removes a portion of the DNA-binding homeodomain (FIG. 6B), does not generate materials. No materials or precipitates were formed by further C-terminal truncation mutants. Therefore, Ubx216-344 likely did not fail due to exposure of a second aggregation-prone region. Within the resolution of the assays, Ubx216-356 is determined as a necessary minimal materials-forming domain. As such, this region must include sequences permitting both fiber formation and fiber-fiber association. Curiously, none of the Ubx sequence features that resemble amyloidogenic or elastomeric proteins in the N-terminal 216 amino acids of the protein were required for materials formation, suggesting alternate mechanisms guide the assembly of materials from this portion of the Ubx sequence.

The decreased robustness of materials produced from Ubx216-356 relative to full-length Ubx indicates that sequences outside this region impact materials assembly, even though these sequences are not absolutely required. The absence of these remote sequences could alter the structure of the materials themselves. However, scanning electron microscopy reveals the surface of ropes composed of Ubx216-356 exhibits the aligned striations characteristic of Ubx ropes. Occasionally, the surface of materials produced from severe truncations appears less smooth and unifor, a trait never observed for ropes created with full-length Ubx. Thus the appearance of Ubx216-356 materials is generally consistent with those composed of Ubx.

Given the architecture of the Ubx216-356 materials generally appears intact, sequences outside this minimal domain must form additional interactions to enhance the robustness of the materials. One obvious mechanism would be for the Ubx sequence to contain a second region capable of forming materials. Any second materials-forming region must lie N-terminal to the first materials forming domain, since removal of amino acids 257-380 does not further hinder materials formation, whereas removal of amino acids 1-216 has a strong impact on assembly. To test this hypothesis, C-terminal truncations, in the context of full length Ubx, were generated (FIG. 6B). Consistent with the existence of a second materials forming domain, ropes were drawn using constructs with longer C-terminal truncations when the N-terminal 215 amino acids were present. Ubx1-243 generated ropes, although they were small and brittle.

Using the Ubx1-243 C-terminal truncation mutant as a template, deletions from the
N-terminus were made to locate the N-terminal boundary of this second materials forming region (FIG. 6B). Ubx19-243, Ubx49-243, and N88-243 generated materials, but not
Ubx139-243. Consequently, the N-terminal minimal materials forming region in Ubx extends from amino acids 88 to 243, overlapping the C-terminal minimal materials forming region by 28 amino acids. Both the N-terminal and C-terminal minimal materials forming regions include the central alanine-rich region (amino acids 221-234). This alanine rich sequence is predicted to form an a-helix whose normal function in transcription activation relies on the potential to form secondary structure. Unfortunately, the N-terminal minimal materials-forming region appears even weaker than the C-terminal minimal materials forming region. Consequently, ropes could not be generated from Ubx88-243 sufficiently long to transfer to an SEM sample holder.

Intriguingly, the N-terminal minimal materials forming region (49-224) does contain the disordered region, most of the GGX and GXXP motifs, and one alanine rich region, and thus its sequence more closely resembles the sequences of known elastomeric, materials-forming proteins. However, the presence of these motifs alone is not sufficient to confer the ability to form the more robust, lengthy ropes. Inclusion of both minimal regions is required to generate long ropes analogous to those generated by the full-length protein.

The following description provides additional methods for the production of a Ubx biomaterial.

Expression of Protein of Interest

Plasmid containing the Ubx gene (or modified version thereof) was transformed into BL21(DE3) PLysS cells and plated on LB-agar containing suitable antibiotics. N-terminally tagged Ubx variants of Ubx chimeras may also be used. Chimeras in which genes are fused to the C-terminus of Ubx do not produce soluble protein. From this plate a single colony was used to inoculate 100 ml of LB containing suitable antibiotics overnight. 10 ml of overnight culture was added to each liter of LB media and grown at 37° C. until OD 0.6-0.8. Cultures were cooled down to expression temperature (between 22-30° C. depending on Ubx or variant) prior to induction. IPTG was added to a final concentration of 1 mM in order to induce Ubx/Ubx-variant expression. 2-3 hours after induction, cells were harvested by spinning at 5000 rpm for 10 mins at 4° C. Supernatant containing LB media was discarded. Cell pellets were resuspended in PBS and stored at −20° C.

E. coli Cell Lysis

The pellets stored at −20° C. underwent 3 freeze/thaw cycles, in which a frozen pellet thaws at room temperature and is refrozen at −80° C. 10 ml of lysis buffer (500 mM NaCl, 1 protease inhibitor cocktail tablet, 1 vial of DNase, 20 µl of BME and 50 mM sodium phosphate buffer, pH 8.0) was added to each liter of cell pellet to form a Lysis Mix. The Lysis Mix was left on ice and a 5 ml plastic pipette was used to mix the pellet with the lysis buffer. It is important to avoid vigorous mixing because it may create bubbles indicative of protein denaturation. As lysis proceeds, solution becomes less viscous: a good indication of the completion of lysis is the formation individual drops when pipetting. This will normally take 20 mins. Excess lysis should be avoided because proteases may destroy our protein of interest. The Lysis Mix was spun at 18,000 rpm for 30 mins at 4° C. to separate protein (supernatant) from other components of the cells (pellet).

Purification Using Nickel Column

Load glass column with Ni-NTA resin (4 ml) and allow the Ni-NTA beads settle down at the bottom. 40 ml of equilibration buffer (5% glucose w/v, 500 mM NaCl and 50 mM sodium phosphate buffer, pH 8.0) was added to the column to equilibrate the resin. The supernatant containing the protein of interest was loaded to the column and allowed to flow through. The column was washed in order to remove proteins other than Ubx that bound to the Ni-NTA beads. Sequential additions of 50 mls of 0 mM, 20 mM, 40 mM and 80 mM of imidazole buffer (each also contains 5% glucose, 500 mM NaCl, 50 µl BME and 50 mM sodium phosphate buffer, pH 8.0) were applied in the order listed. Ubx/variants were eluted from the column using 20 ml of elution buffer (200 mM imidazole, 5% glucose, 500 mM NaCl and 50 mM sodium phosphate buffer, pH 8.0) and collected in 1-2 ml fractions. DTT (approx. 10-20 mg) was added to preserve protein at 4° C. If using EGFP-Ubx or mCherry-Ubx, the elution fraction should be green, and if not should develop the green color in a few hours as a result of the oxidation.

Purification of Un-Tagged Ubx

Ubx may also be purified by ion exchange followed by Ni-NTA chromatography.

Production of Ubx-Based Materials:

Ubx Film

Ubx protein solution was diluted to 0.6 mg/ml using elution buffer (200 mM imidazole, 5% glucose w/v, 500 ml NaCl and 50 mM sodium phosphate buffer, pH 8.0). Undiluted, impure Ubx (cleared cell lysate) will also produce materials. Ubx solution (100 µl) was placed on the surface of a siliconized coverslip at room temperature. Ubx film spontaneously forms at the air-water interface after approximately 1 hour.

Ubx Fiber

Objects with sharp ends (pipette tip, needle etc.) were used to gently contact the surface of Ubx film. Objects with sharp ends were withdrawn slowly to draw ropes. The length of the fiber drawn is proportional to the surface area of the film. By rough estimation, 5 cm of fiber may be made from a 100 µl drop with a surface area of 0.5 $cm^2$. Ropes are stored under tension by spanning across two parallel stems of paper clips.

Ubx Sheet

Ubx protein samples were concentrated to 1 mg/ml using Vivaspin concentrators with a 10 kD cut off (Viva Science). EDTA was added to Ubx protein samples to a final concentration of 10 mM. 100 µl of Ubx solution (1 mg/ml, 10 mM EDTA) was placed at the surface of a siliconized coverslip forming a drop. The drop was covered with a 15 ml falcon tube cap to deter evaporation and contamination. Ubx sheets formed spontaneously at the air-buffer interface at room temperature overnight.

Ubx Lattices

The outer turn of a paperclip, in which the inside turn had been bent out of the way, was used as a support for lattice construction. Ubx ropes were wound around the parallel arms of an opened paper clip such that the ropes intersect between the supporting arms. Freshly made Ubx ropes would adhere to both the metal supports and to each other, forming a lattice. Ubx lattices harden over time: freshly made lattices are flexible, upon drying in the air for 24 hours, lattices harden and may maintain their form after removal from the support.

Ubx Bundle

A dome-shaped 20 µl drop of deionized water was placed on the surface of a siliconized cover slip. A series of Ubx ropes were placed in parallel, approximately 1 mm apart, on the paper clip support, and subsequently dipped into the drop of water. The series of Ubx ropes were slowly withdrawn during which interactions with the shrinking water surface pull the ropes toward the middle of the series, where the ropes adhere to each other, forming a multi-fiber bundle. The degree to which the ropes fuse in the bundle appears to be dependent on the age of the ropes: the fresher the ropes, the larger degree of fusion would be observed.

Ubx Tethered Encapsulates: Microbaskets

Ubx sheets were prepared as described. Objects with sharp ends (pipette tip, needle etc.) were used to make contact with the surface of the sheet and slowly withdrawn to produce mini-encapsulated baskets.

Ubx Tethered Encapsulates: Macrobaskets

Ubx purification was performed as described. A peak concentration of approx 2 mg/ml during elution is required. At the elution step, the flow rate of elution was adjusted to be extremely slow using a plastic two-way stopcock to enable the formation of Ubx macro-encapsulated baskets. Both types of Ubx tethered encapsulates hardens overtime: freshly made encapsulates are flexible, upon drying in the air for 2-3 days, the encapsulate shrinks and hardens.

Alternate Methods for Film, Fiber, and Sheet:

Generating films, ropes, and sheets from sessile drops appeared to be hampered by two problems. First, the drops could dry before materials assemble, especially with slower Ubx variants. Second, sudden movement could fracture ropes and sheets when pulling or lifting them by hand. To circumvent these problems, a materials-generating instrument was constructed. Ropes generated by this method were stronger and more extensible.

A reservoir (approx. 17 cm×22 cm×1 cm) was filled with lysis buffer without DNase I or proteinase inhibitor such that the meniscus was inverted above the rim of the reservoir. A much larger reservoir containing 4 L of buffer has also worked. Between 200 to 500 µl of Ubx (or Ubx variant) protein were added into the reservoir. The system was incubated at room temperature for approximately 4 hours. The liquid surface was compressed by setting two Teflon blocks on the edge of the reservoir and slowly pushing them toward the center. To generate fibers, a motor was used to slowly turn an axle and lower the needle into the liquid. Reversing the direction of the motor slowly withdrew the needle from the surface and pulled a fiber. To generate film, a thin piece of plastic, in lieu of a needle, was dipped in the protein solution using the motor and axle. Fibers and/or film may also be pulled from this reservoir by hand.

Buffer List

Lysis buffer (5% glucose w/v, 500 ml NaCl, 1 protease inhibitor tablet (Roche), 0.8 mg/L DNase I and 50 mM sodium phosphate buffer, pH 8.0). Equilibration buffer (5% glucose w/v, 500 ml NaCl and 50 mM sodium phosphate buffer, pH 8.0). W1, W2 and W3 buffer (20 mM, 40 mM and 80 mM imidazole, respectively, dissolved in equilibration buffer and adjusted to pH 8.0). Elution buffer (200 mM imidazole dissolved in equilibration buffer). Freezing buffer (5% glucose w/v, 300 mM NaCl, 1 mM DTT and 50 mM sodium phosphate buffer, pH 7.5).

The ability of Ubx to form materials may be affected by the buffer. For example, the salt concentration is important (Ubx at lower salt amorphously aggregates rather than assembles into ordered materials). In some cases, EDTA seems to help prevent amorphous aggregation. The source of the issue may be nickel leaching from the Ni-NTA column and is related to resin storage/shipping. Finally, if glycerol is substituted for glucose, one may still assemble materials (as monitored by the ability to pull ropes), but not as easily (ropes are shorter).

Features of Ubx Materials:

The Ubx gene is stable in E. coli so one may easily produce Ubx monomers (unlike genes for elastin, spider silk, mussel adhesive protein). Ubx self-assembles at the air-water interface near neutral pH in a buffer in which most proteins are expected to be stable. Assembly methods for artificial proteins based on silk and/or elastin typically require denaturants, heat, low pH, organic solvents, or other conditions that would denature or aggregate most proteins. These harsh assembly conditions will limit the ability to incorporate novel functions by fusing a gene for a functional protein with the gene for the materials-producing protein to generate a protein chimera. The added protein would likely denature and loose function or drive amorphous aggregation in competition with materials formation in the harsh conditions used in the prior art. One may generate materials from protein fusions, in which the added protein is active (green and red fluorescent ropes). One may pattern materials using multiple Ubx variants (e.g., EGFP-Ubx and m-Cherry-Ubx). The materials are self-adhesive, allows building complex macroscale structures. A biomaterial may be stored dry for greater than one year (a fiber pulled Feb. 1, 2007 is available). A biomaterial may be shipped dry with minimal damage (4 our of 5 fibers arrive after shipping by UPS). A surface of a biomaterial may be coated, for example, with antibody-conjugated nanoparticles.

Example 7

Size May Dictate Mechanical Properties of Ubx Fibers

Ubx fibers were created as described below and by controlling diameter, the mechanical properties were measured as a function of fiber diameter. Controlling fiber size may be a facile way to manipulate the mechanical characteristics of protein fibers, to mimic the properties of natural materials, and to rationally engineer macroscale protein-based materials and structures with desired properties.

Methods

Expression and Purification of Ubx.

The ubx mRNA is alternatively spliced in vivoand the Ubxla isoform (termed Ubx in this document) was used in this study. The ubx gene had previously been cloned into the pET-19b vector between the NdeI and BamHI sites to create pET-19b-Ubx. Ubx was purified from the E. coli strain BL21(DE3)pLysS transformed with pET-19b-Ubx.

Generation of Ubx Fibers.

Figure 7A:
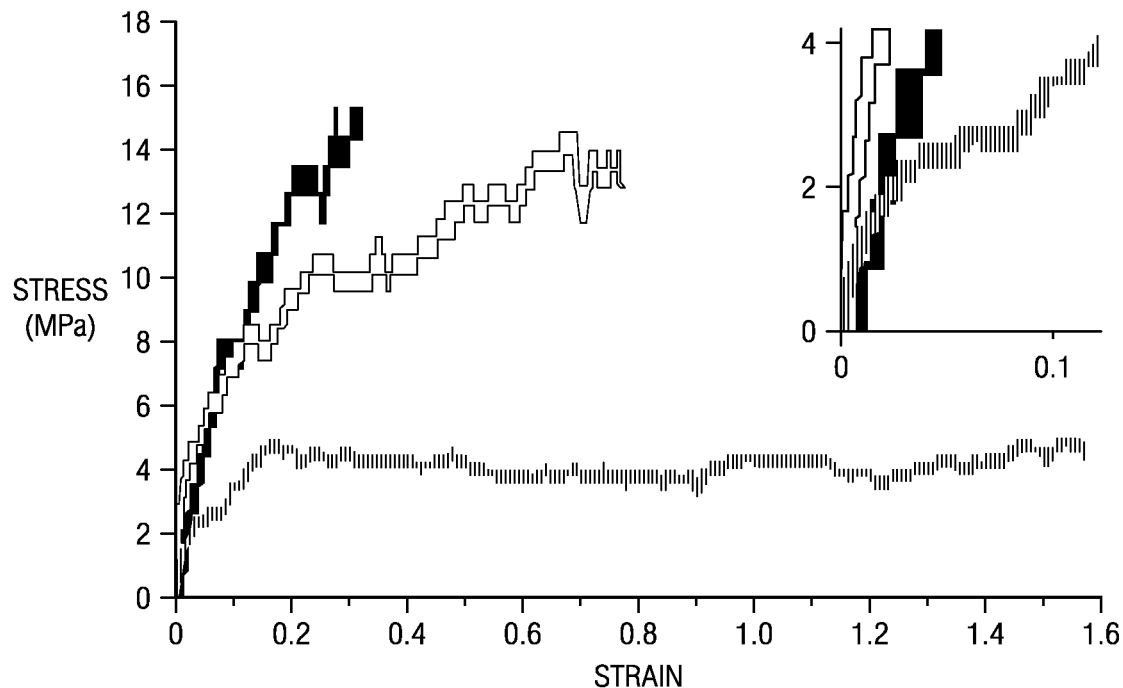
FIGS. 7A-7G illustrates the impact of diameter on the mechanical properties of Ubx fibers according to specific example embodiments of the disclosure.
Figure 7B:
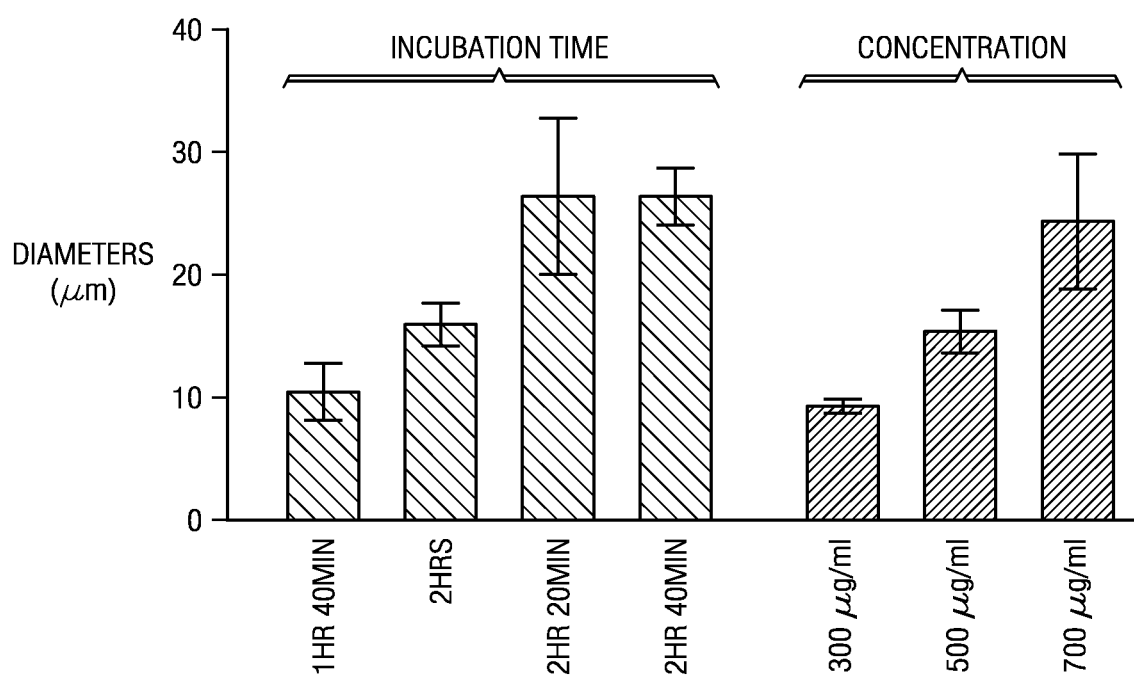
Figure 7C:
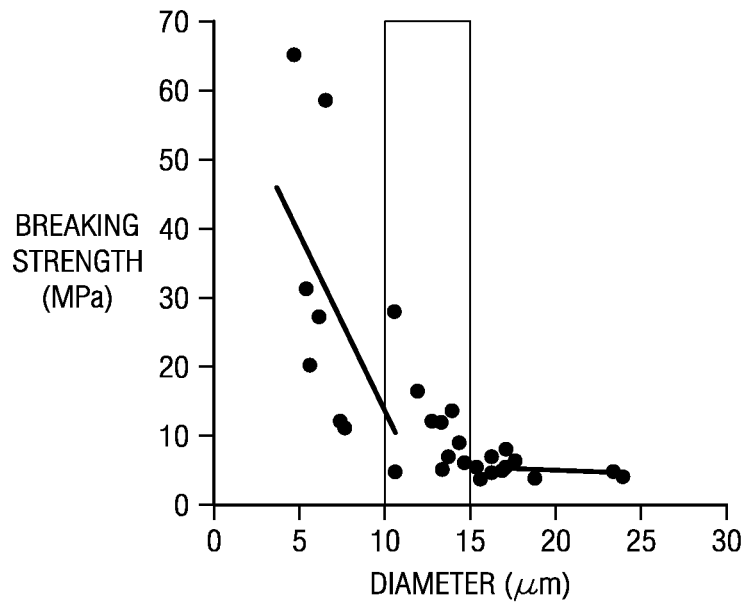
Figure 7D:
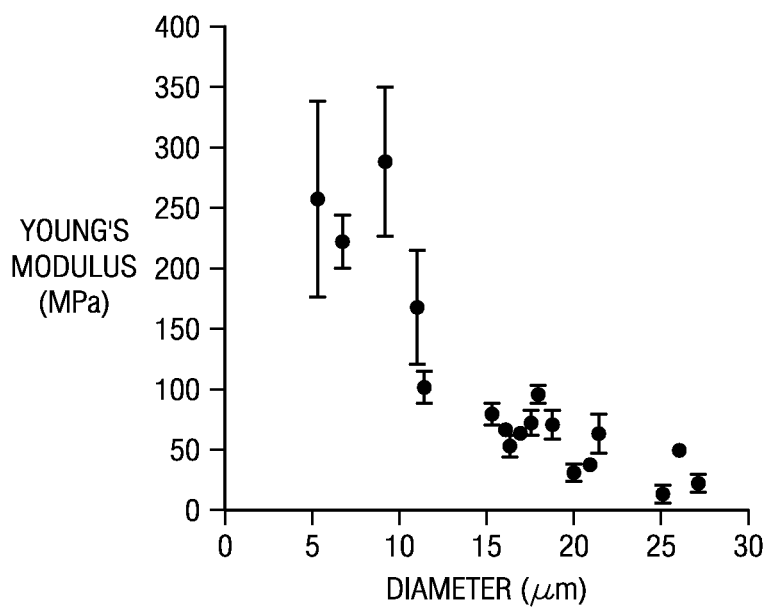
Figure 7E:
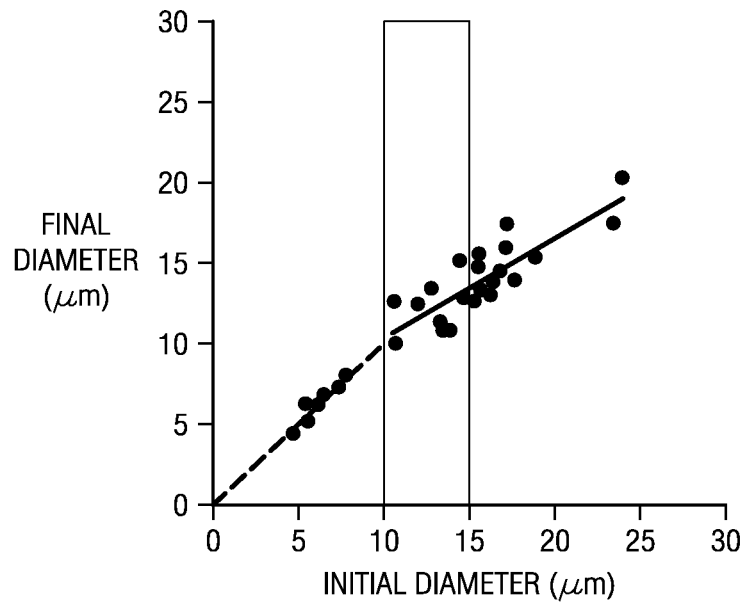

Ubx in solution spontaneously generates a film composed of nanoscale fibrils at the air-water interface, and Ubx fibers are drawn from this film. To generate fibers with a defined diameter, the protein concentration and the incubation time for film formation were adjusted. The influence of both concentration and incubation time on fiber diameter is shown in FIG. 7b.

Mechanical Testing.

A Gatan Microtest™ tensile tester was used to characterize the mechanical properties of Ubx fibers. The load cell had a 2 N load capacity. The sensitivity of the load cell is 0.0001N, and the force sensitivity of the extensometer is 0.001 mm. When not otherwise specified, a loading speed of 0.1 mm/min was used, to mitigate pulling rate effects on the measurements. The data sampling rate was 500 ms. Samples were attached to double sided carbon sticky tape on the clamps using Loctite 495™ adhesive. Since individual fibers have very uniform diameters, and the use of fibers in scanning electron microscopy experiments precludes their subsequent use in mechanical testing, fibers were cut into two sections, one for measurement of the initial sample diameter by SEM, and one for tensile experiments followed by measurement of the final sample diameter. In order to accurately measure the Young's modulus of these protein fibers, multiple highly consistent unloading-loading curves in each successful tensile test were used, since only elastic deformation could be recovered during unloading. The average slope of these unloading curves provides a much more accurate estimation of sample Young's modulus by avoiding uncertainties related to the initial sample alignment and the settling process in the early part of the tensile tests. For wide fibers, Young's modulus was measured using unloading curves after the yield point.

The Gatan Microtest™ tensile tester is also vacuum compatible and has been modified to be used inside a FEI quanta 400™ scanning electron microscope. This experimental arrangement enables in situ tensile tests of the selected protein fibers with sufficient hydration, allowing observation of the deformation process in real time during a quantitative tensile test and linkage of specific behaviors to corresponding stress or strain values.

Results

Size influences both the magnitude of mechanical properties and the mechanism of extension of Ultrabithorax (Ubx) fibers. For narrow Ubx fibers, <10 μm diameter, extension is largely elastic, with the breaking strength and Young's modulus decreasing sharply with increasing diameter, whereas the predominantly plastic deformation of wide fibers (>15 μm diameter) reflects the increase in breaking strain with increasing diameter. Wide fibers contain an elastic core, causing the plastically deformed outer layers to wrinkle upon unloading.

Alternately, robust fibers may be generated that are composed of longitudinally aligned fibrils and have diameters between 2 and 50 μm. Furthermore, these basic structures may be manually fused to generate more complex architectures, such as fiber bundles, twists, lattices, and tethered encapsulates (which are a combination of sheet and fiber).

Fibers with diameters less than 10 μm deform elastically, whereas wider fibers (>15 μm) appear to be constructed of multiple layers, in which the outer layers primarily undergo plastic deformation. Consequently, diameter may be varied to alter not only the magnitude of the mechanical properties, but also the mechanism by which the fibers extend. Controlling diameter generated Ubx fibers with an extensibility and strength matching natural elastin.

In testing the mechanical properties of Ubx materials, Ubx fibers were surprisingly extensible, although the breaking strain (53%±19%) and the shape of the stress-strain curves varied significantly between samples. The shapes of the stress-strain curves parse into three groups based on the diameter of the Ubx fiber. Whereas the diameter of an individual fiber along its length is quite uniform, diameter varies significantly between fibers. The stress on narrow fibers (<10 μm) increases nearly linearly with increasing strain, suggesting elastic deformation (FIG. 7a). In contrast, the stress-strain curves of wide fibers (>15 μm) have a yield point indicative of an elastic-to-plastic transition. Stress-strain curves for third group, fibers with a diameter between 10 and 15 μm, are intermediate between these two extremes. Importantly, wide fibers rupture at much higher strains than narrow fibers, potentially explaining the observed wide variation in breaking strain.

Further experiments demonstrate that fiber diameter may be controlled by altering either the amount of time allowed for film assembly or by changing the concentration of Ubx monomers used for film self-assembly (FIG. 7b). Longer incubation time or increased protein concentration increases fiber diameter, presumably by increasing the density of fibrils in the film from which the fiber is drawn. The ability to control fiber diameter enabled a systematic study to determine the impact of fiber diameter on the mechanical properties and mechanism of deformation.

By examining a range of fiber diameters, the differences in the shape of the stress-strain curves originate from changes in the diameter-dependence of key mechanical properties (FIG. 7). For narrow fibers, the breaking strength is strongly dependent on diameter: a two-fold increase in diameter is sufficient to decrease the breaking strength several-fold. Consequently, the Young's modulus of narrow fibers also decreases sharply with increasing diameter. This trend is similar to that observed for elastin-like peptides, further suggesting that the deformation of narrow fibers is primarily elastic. Indeed, typical stress-strain curves for narrow fibers show little sign of non-recoverable change (FIG. 7a), a fact further confirmed by the consistency of a series of loading/unloading curves on a single narrow fiber used to determine Young's modulus (data not shown). Furthermore, the initial diameter of narrow fibers is nearly identical to the fiber diameter after rupture, despite the fact that narrow fibers were extended to an additional ~40% of their initial length before breaking (FIG. 7f). Finally, we observed no evidence of necking at the rupture point (data not shown), suggesting elastic deformation is the predominant deformation mode in these narrow fibers.

In contrast, for wide fibers—with a diameter greater than 15 μm—both the breaking strength and Young's modulus are largely independent of diameter (FIG. 7). However, the breaking strain increases rapidly with increasing diameter for wide fibers, even though, for narrow fibers, breaking strain is independent of diameter. As noted above, typical stress-strain curves for wide fibers shows a distinctive "yielding" behavior after the initial elastic deformation (FIG. 7A), suggesting the occurrence of large scale, non-recoverable plastic deformation or rearrangement of fibrils within fibers (up to 150% extensibility). Such rearrangement could account for the surprising extensibility of wide fibers. The extent of plastic deformation increases with increasing fiber diameter, with the widest fibers able to sustain the most strain (FIG. 7). Wide fibers do not return to their initial diameter after rupture (FIG. 7E), a further indication of plastic deformation. The magnitude of this trend increases with increasing diameter. Finally, lower breaking strain and breaking strength is observed at faster pulling rates for wide fibers, suggesting fibrils within the fibers lack sufficient time to rearrange at faster pulling rates.

Figure 7F:
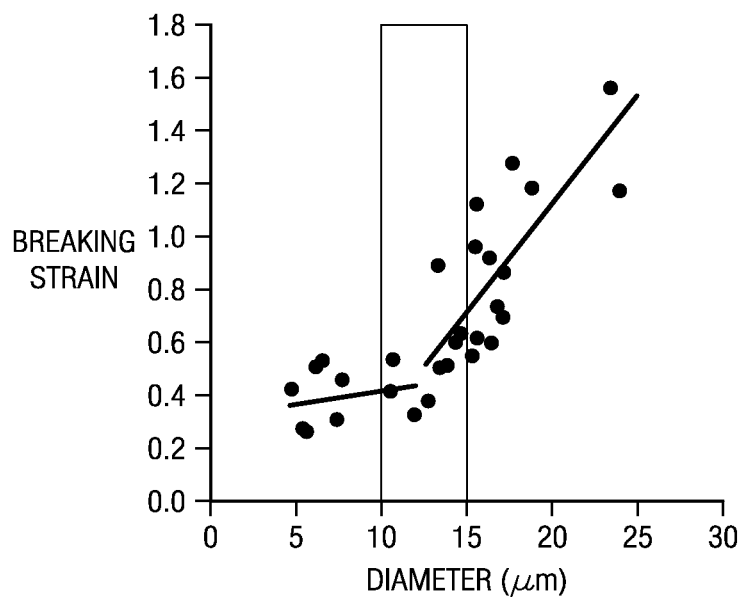
Figure 7G:
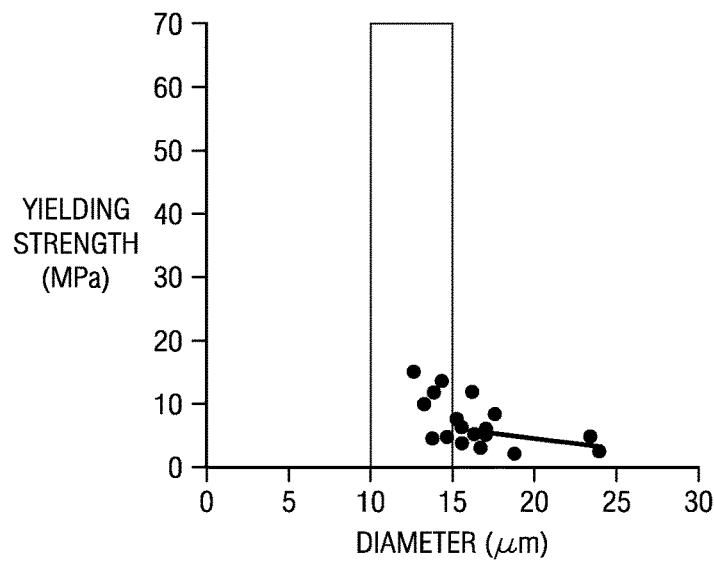

Fibers having diameters between 10 and 15 μm, have mechanical properties between the extremes of those for narrow and wide fibers. The presence of both elastic and plastic traits in these intermediate fibers, combined with the fact that wide fibers initially deform in an elastic manner (FIG. 7A), demonstrates that even wide fibers deform, to some extent, in an elastic manner. Arrangements by which wide fibers may incorporate both properties include: i) wide fibers might contain a heterogeneous mixture of fibrils, some of which deform elastically and some of which deform plastically, ii) wide fibers might contain small occlusions or defects, around which fibers may locally rearrange under strain in order to fill gaps, or iii) wide fibers might be partitioned into an elastic core surrounded by one or more plastically deforming layers. Given each fiber is drawn from a single film constructed of fibrils, it seems extremely unlikely that the uniform conditions used to produce fibers and film would results in a heterogeneous mixture of fibrils, and, moreover, that plastically deforming fibrils would be incorporated into wide fibers yet excluded from narrow fibers. Furthermore, this biphasic response of the mechanical properties to diameter is not primarily due to nonhomogeneous or local responses to tensile stress, since fibers before and after fracture have a uniform diameter. Therefore, these data best fit a model in which the core of the wide fibers undergoes elastic deformation, and provides most of the tensile strength of the fiber. The outer shell of wide fibers consists of layers of fibrils capable of plastic rearrangements in response to tensile loading. Since wider fibers have thicker outer layers, they would have more fibrils available for plastic rearrangement and thus be able to undergo larger strains without rupturing (FIG. 7F). This model predicts that wide fibers should wrinkle upon unloading, as the elastic core returns to its original length and the plastically deformed outer layers retain the longest length acquired under tensile stress. Furthermore, this model correctly predicts multiple aspects of the behavior of wide fibers under tensile stress.

Example 8

Biomaterials

Figure 8:
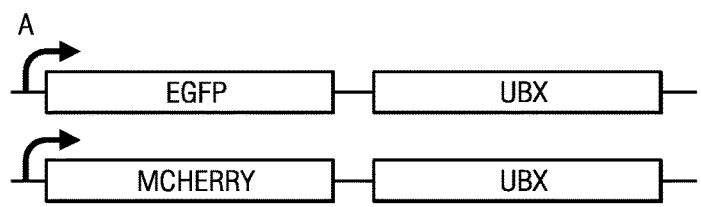
FIG. 8 illustrates fluorescent marker-Ubx fusion proteins according to specific example embodiments of the disclosure.

A key advantage of protein-based materials, according to some embodiments, is the potential to directly incorporate novel functions via gene fusion to produce chimeric polypeptides capable of both self-assembly and the desired chemical reactivity. However, facile production of functionalized protein materials may be hampered by the need to generate recombinant chimeric monomers and/or the requirement to assemble the materials in conditions that will not irreversibly damage the functional protein. In contrast, the gene encoding the Drosophila melanogaster transcription factor Ultrabithorax (Ubx) is stable in E. coli, and the recombinant protein rapidly self-assembles in gentle, aqueous conditions to form materials with a variety of morphologies. Ubx chimeras incorporating either Enhanced Green Fluorescent Protein (EGFP) or mCherry generate fluorescent materials, demonstrating the activities of the functional proteins are neither impaired by the assembly process nor by confinement within the material (FIG. 8). The chimeric protein illustrated contains a histidine tag, followed by EGFP, which is separated from the subsequent Ubx amino acid sequence by a single glycine amino acid which acts as a spacer. Other arrangements or spacings between EGFP and Ubx may also be effective. The procedures for protein expression, purification, and assembly for the chimeric proteins are the same as for his-tagged Ubx. These chimeric proteins may provide additional advantages over materials constructed only from Ubx (e.g., increased expression and/or improved visualization). For example, adding EGFP or mCherry to Ubx increases the expression of Ubx in E. coli and makes the expressed material easier to locate and track in liquids or in cell cultures.

Figure 9:
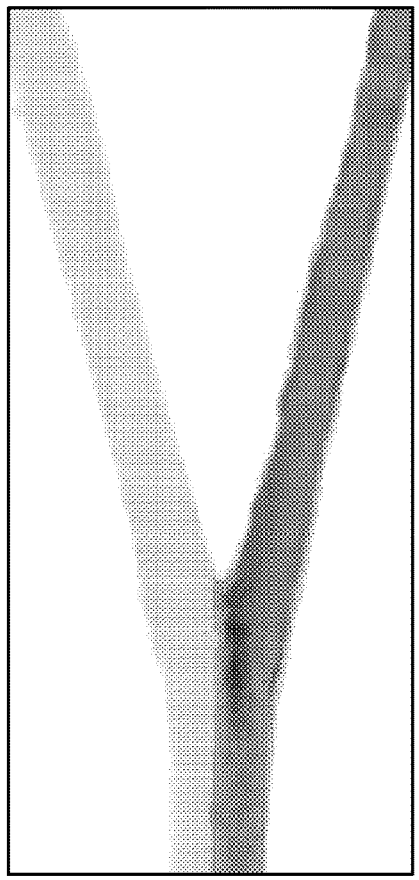
FIG. 9 illustrates bundled ropes using two different fluorescent protein marker-Ubx fusion proteins (mCherry-Ubx, left; EGFP-Ubx, right) according to a specific example embodiment of the disclosure.

EGFP-Ubx and mCherry-Ubx monomers, according to some embodiments, may be combined to self-assemble patterned materials. Self-adhesive properties of Ubx materials may also permit manual construction of microscale to macroscale patterned materials. For instance, a fiber constructed with the EGFP-Ubx chimera may be fused to a fiber constructed with the mCherry-Ubx chimera to create a "mixed bundle" that fluoresces green on one face and red on the other (FIG. 9). On either end of the bundle, the fibers remain separated. Likewise, twists, lattices and other three dimensional structures may be manually generated using separately drawn green and red fluorescent fibers.

Using the "drop on a surface" method of generating materials, fibers may be drawn already imbued with particular patterns (FIG. 10). To self-assemble pre-patterned fibers, a drop of EGFP-Ubx is incubated adjacent to, but not touching, a drop of mCherry-Ubx at room temperature for approximately one hour. This incubation time allows films to separately form without allowing EGFP-Ubx and mCherry-Ubx to mix by diffusion, which would create a less distinct boundary between the two colors. Following this pre-incubation step, the two drops are allowed to come into contact with one another, and they are incubated for a further one hour to allow the green and red fibrils to adhere. These two incubation times may be varied significantly, or EGFP-Ubx and mCherry-Ubx may be in contact throughout a single long incubation. At this point, fibers may either be drawn as "faced fibers" or with vertical stripes. Fibers drawn from the center of the red/green boundary will pull as faced fibers, which, like the mixed bundle, have a green face and a red face (FIGS. 10A and 10B). Unlike the mixed bundle, faced fibers may have a narrower diameter since they are composed of only a single fiber, and the red and green components are not separated at the fiber termini. Fibers with vertical stripes may be drawn by alternately pulling from the green or red drops (FIGS. 10C and 10D). A large (200 µl) drop of EGFP-Ubx was placed on a siliconized coverslip and left to assemble a film for 2 hours. Subsequently, small amounts of mCHerry-Ubx (either 0.5 µl or 1.0 µl was used) were placed at distinct locations on the surface, and the unstirred mixture allowed to assemble for a further 10 minutes. Fibers pulled from this mixed film were largely comprised of EGFP-Ubx, but contained spots enriched in mCherry-Ubx (FIGS. 10E and 10F).

What is claimed is:

1. A method of making a biomaterial comprising a Ubx protein, the method comprising:
   a) exposing an aqueous buffer comprising Ubx monomers to air,
   b) allowing oligomerization of the Ubx monomers to occur at the air-water interface of the aqueous buffer to form a biomaterial;
   c) recovering the biomaterial.

2. The method of claim 1, wherein the aqueous buffer is a non-denaturing aqueous solution having a pH of about 6 to about 8.

3. The method of claim 1, wherein oligomerization occurs at a temperature of about 25° C. or lower.

4. The method of claim 1, wherein the aqueous buffer contains NaCl, sodium phosphate, and glucose.

5. The method of claim 1, wherein the the biomaterial is a fibril, film, fiber, sheet, bundle, lattice, or encapsulate.

6. The method of claim 1, wherein the aqueous buffer comprising Ubx monomers is a concentrated Ubx protein solution.

7. The method of claim 1, wherein oligomerization occurs in less than about 10 hours.

8. The method of claim 7, wherein oligomerization occurs in about one to about five hours.

9. The method of claim 1, wherein the aqueous buffer comprising Ubx monomers is placed in a covered chamber.

10. The method of claim 1, wherein recovery of the biomaterial comprises contacting the air-water interface of the aqueous buffer with a surface, wherein the contacting results in adherence of the biomaterial to the surface.

11. The method of claim 1, wherein the biomaterial comprises Ubx fibrils having a diameter from about 2 to about 50 µm.

* * * * *